United States Patent [19]

Kikuchi et al.

[11] Patent Number: 5,641,485
[45] Date of Patent: Jun. 24, 1997

[54] CALEDOTHRICINS USED IN THE TREATMENT MYCOTIC DISEASES

[75] Inventors: Masae Kikuchi, Tokyo; Hisao Shimada, Fujisawa; Hitomi Tanaka, Yokohama, all of Japan

[73] Assignee: Hoffmann-La Roche Inc., Nutley, N.J.

[21] Appl. No.: 514,019

[22] Filed: Aug. 11, 1995

[30] Foreign Application Priority Data

Aug. 17, 1994 [EP] European Pat. Off. ............ 94112790

[51] Int. Cl.$^6$ .................. A61K 35/74; C12P 1/04
[52] U.S. Cl. ........................... 424/122; 435/170
[58] Field of Search ................. 424/122; 435/170

[56] References Cited

U.S. PATENT DOCUMENTS

| | | | |
|---|---|---|---|
| 4,062,943 | 12/1977 | Lindberg | 424/115 |
| 4,277,462 | 7/1981 | Strobel | 424/115 |
| 4,342,746 | 8/1982 | Strobel | 424/115 |
| 4,377,571 | 3/1983 | Strobel | 424/115 |

*Primary Examiner*—Jerome D. Goldberg
*Attorney, Agent, or Firm*—George W. Johnston; Ellen Ciambrone Coletti; Robert A. Silverman

[57] ABSTRACT

Physiologically active caledothricins A–I and their salts, which are useful for the treatment of mycotic diseases. Also strains belonging to the genus Pseudomonas capable of producing the caledothricins upon cultivation.

10 Claims, 10 Drawing Sheets

CALEDOTHRICINS USED IN THE TREATMENT MYCOTIC DISEASES

BACKGROUND OF THE INVENTION

1. Field of Invention

The invention relates to physiologically active caledothricins and their salts, and microorganisms having the ability to produce the caledothricins in a culture medium.

2. Background

Deep mycosis by opportunistic fungi in immunocompromised patients have been increasing due to a variety of predisposing factors such as AIDS, cancer theraphy, organ transplantation, increase of the aged population and increased use of antibiotics. In these immunocompromised patients, a number of fungi that are not pathogenic in healthy human behave as virulent pathogens. As a result, there is a rapidly increasing medical need for well-tolerated antifungals. However, well-tolerated antifungals have not yet been fully developed. Only a few antifungals for systemic mycoses are on the market. Moreover the properties of these antifungals do not meet practical needs to full extent.

SUMMARY OF THE INVENTION

We prepared caledothricins A, B, C, D, E, F, G, H, and I, described below, by cultivating strains belonging to the genus Pseudomonas and identified as Pseudomonas spp. BA 7399 and BA 8429. We found that caledothricins A, B, C, D, E, F, G, H, and I and their salts possess broad antifungal spectra, and are useful for the treatment of mycotic diseases.

BRIEF DESCRIPTION OF THE DRAWINGS

Caledothricins A, B, C, D, E, F, G, H, and I according to the invention will be described with reference to the accompanying drawings in which.

DETAILED DESCRIPTION OF THE INVENTION

The physico-chemical properties of the physiologically active caledothricins A, B, C, D, E, F, G, H and I are as follows:

Caledothricin A:

1) Appearance: white solid

2) Specific rotation: $[\alpha]^{24}D-50.8°\pm6.4°$ (c=0.10, in pyridine)

3) Molecular weight (FAB-MS method)

Positive ion mode: m/z 1401 (M+H)$^+$, 1423 (M+Na)$^+$

Negative ion mode: m/z 1399 (M-H)$^-$, 1417 (M+H$_2$O—H)$^-$

4) Molecular formula: $C_{65}H_{100}N_{12}O_{22}$

5) High resolution mass spectroscopy (for M+H):

Found: 1401.7117 Calcd. for $C_{65}H_{101}N_{12}O_{22}$:1401.7143

Figure 1:
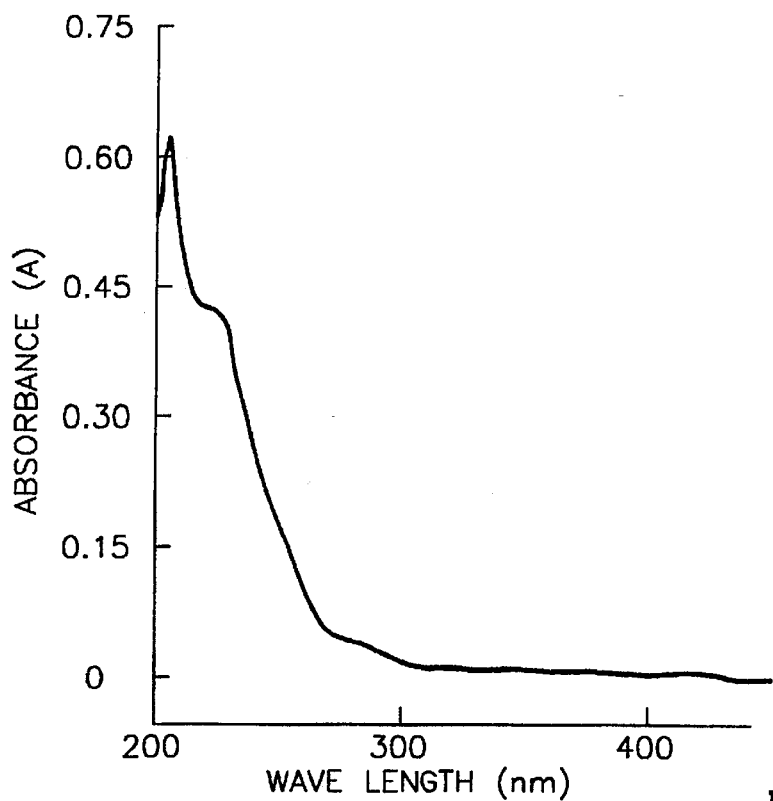
FIG. 1 shows the UV spectrum of caledothricin A.

6) UV spectrum: in methanol (See FIG. 1)

$1_{max}$ 203±5 (ε4300), 224±5 (ε2900 sh), 275±5 (ε280 sh) (in methanol)

$1_{max}$ 203±5 (ε3500), 220±5 (ε2900 sh), 275±5 (ε315 sh) (in N/10HCl-methanol)

$1_{max}$ 204±5 (ε7200), 225±5 (ε2600 sh), 245±5 (ε1600 sh), 295±5 (ε200 sh) (in N/10NaOH-methanol)

Figure 2:
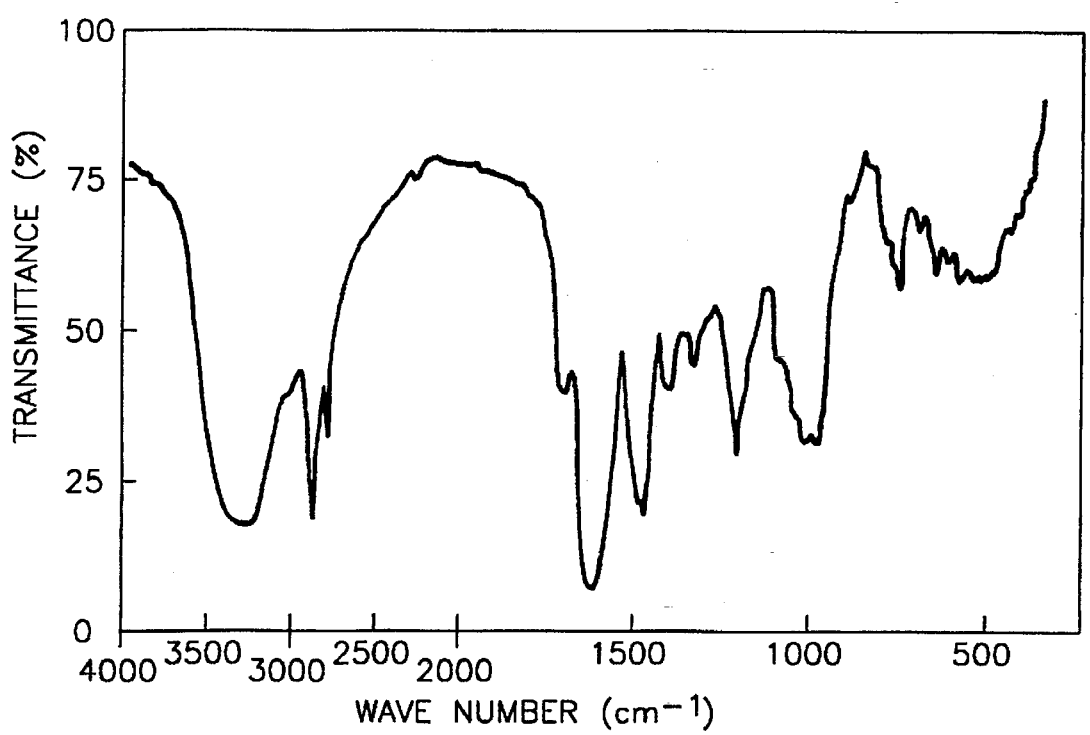
FIG. 2 shows the IR spectra of caledothricin A.

7) IR spectrum: in KBr tablet (See FIG. 2)

Figure 3:
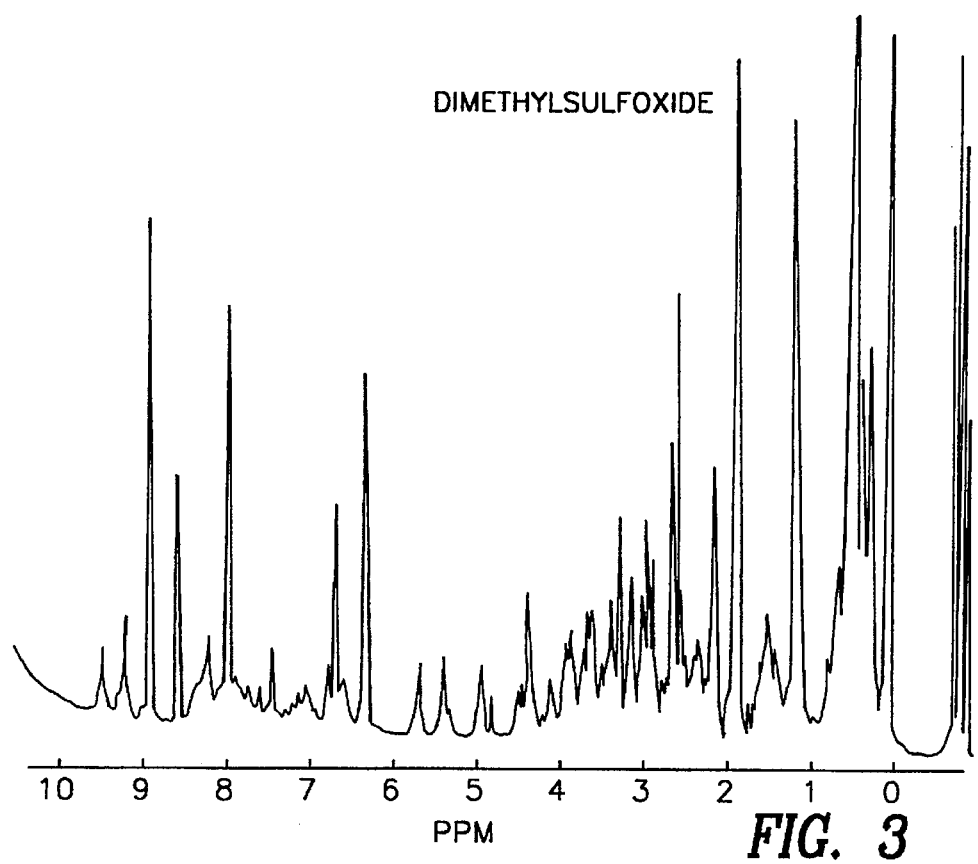
FIG. 3 shows the $^1$HNMR spectra of caledothricin A.

Main absorption wavenumbers (cm$^{-1}$) are as follows: 3298, 2925, 2854, 1745, 1657, 1517, 1262, 1100–1000, 8) $^1$H-NMR spectrum: 400 MHz, in mixture of dimethylsulfoxide-d$_6$ and trifluoroacetic acid (25:1) (See FIG. 3)

Figure 4:
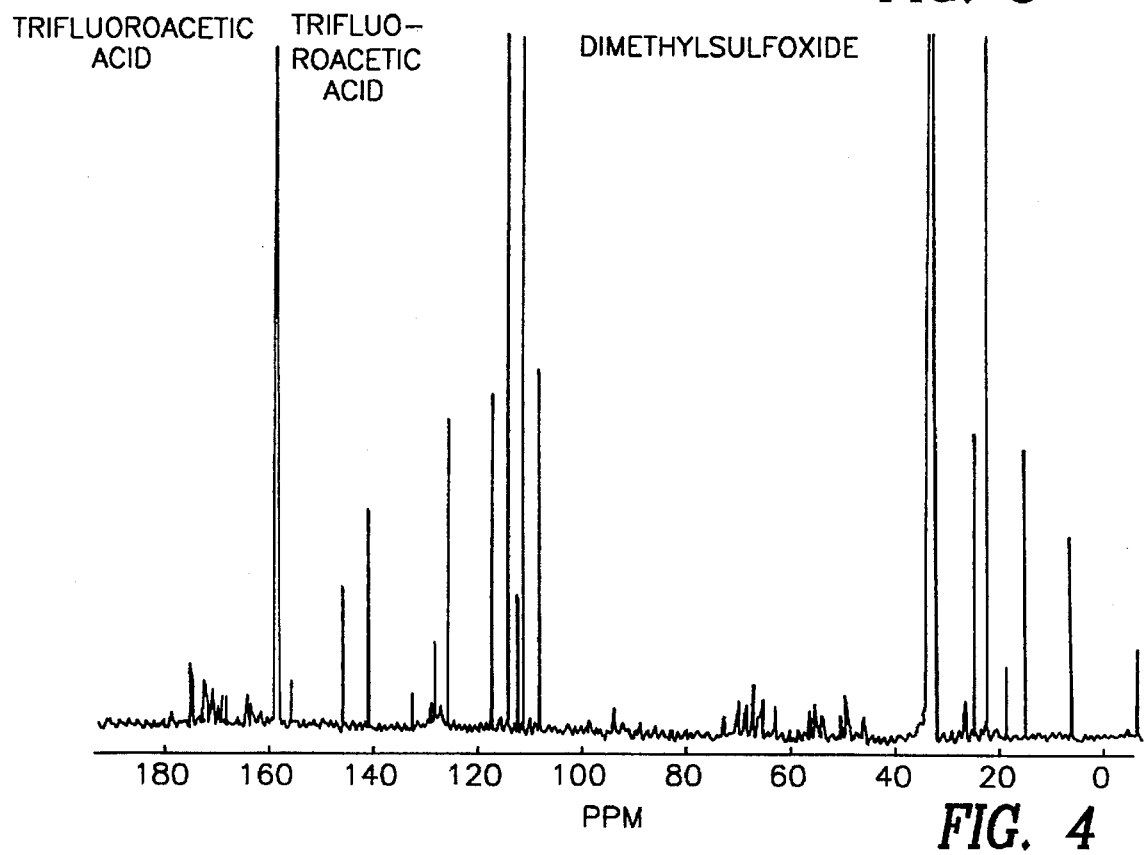
FIG. 4 shows the $^{13}$C-NMR spectra of caledothricin A.

9) $^{13}$C-NMR spectrum: 100 MHz, in mixture of dimethylsulfoxide-d$_6$ and trifluoro acetic acid (25:1) (See FIG. 4.)

10) Solubility:

Soluble: pyridine, trifluoroacetic acid,

Sparingly soluble: water, dimethyl sulfoxide, methanol

11) Color reaction:

Positive: Anisaldehyde-sulphuric acid, HBr-ninhydrine, iodine vapor, molybdophosphoric acid, vanillin-sulphuric acid, Rydon-Smith reagent Negative: bromocresol green, ferric chloride, 2,4-dinitrophenyl-hydrazine-sulphuric acid, Sakaguchi reagent, silver nitrate 12) Thin-layer chromatography (TLC)

| Carrier | Solvent system | Rf |
|---|---|---|
| silica gel F254*[1] | dichloromethane:methanol:water (60:35:5) | 0.13 |
| | n-butanol:acetic acid:water (3:1:1) | 0.25 |

*[1]E. Merck AG., Germany

13) High Performance Liquid Chromatography (HPLC):

Carrier: >YMC-PAK<A303, a reversed phase silicagel $C_{18}$ column for HPLC manufactured by Yamamura Chemical Laboratories Mobile phase: Acetonitrile: 10 mM Sodium hydrogen phosphate buffer (pH 3.4)=45:55

Flow rate: 1 ml/min. Rt=16.3±0.5 min

14) Classification of substance: amphoteric substance

15) Amino acid analysis: Caledothricin A was heated at 120° C. in 6N HCl for 24 hours, followed by subjecting to amino acid analysis to detect tyrosine, threonine×2, glutamine, glycine, histidine.

Caledothricin B:

1) Appearance: white solid
2) Molecular weight (FAB-MS method)
Positive ion mode: m/z 1223 (M+H)$^+$
Negative ion mode: m/z 1221 (M−H)$^−$,
3) Molecular formula: $C_{59}H_{90}N_{12}O_{16}$
4) IR spectrum: in KBr tablet (See FIG. 5)

Figure 6:
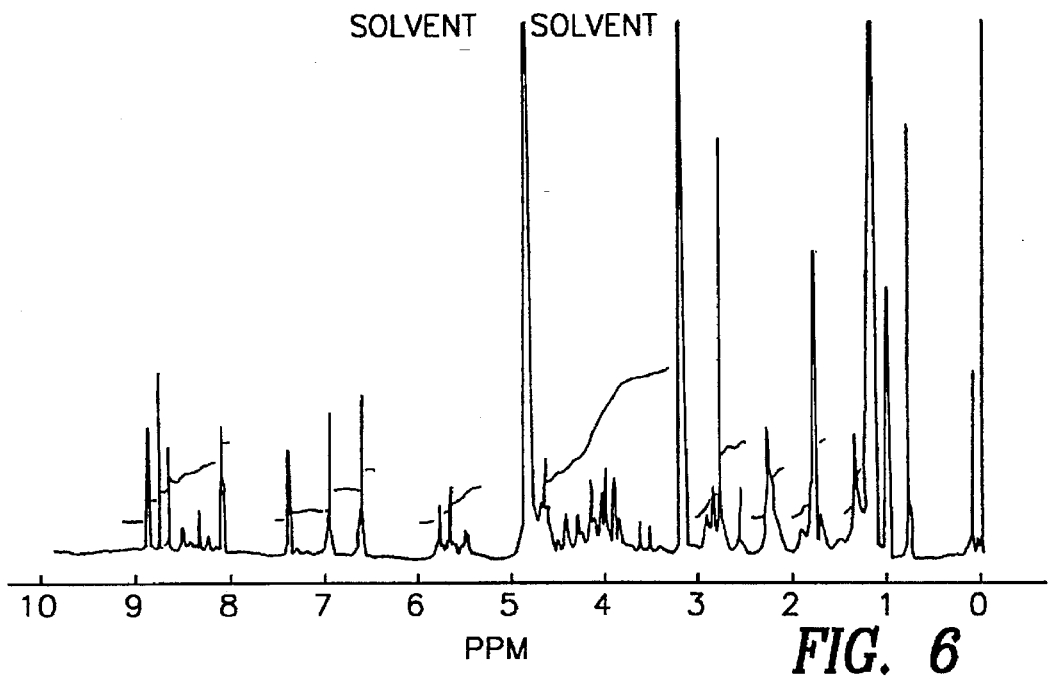
FIG. 6 shows the $^1$H-NMR spectra of caledothricin B.

Main absorption wavenumbers (cm$^{-1}$) are as follows: 3304, 2926, 2854, 1741, 1657, 1518, 1261, 1130–1060, 5) $^1$H-NMR spectrum: 400 MHz, in mixture of dimethylsulfoxide-d$_6$ and trifluoroacetic acid (25:1), (See FIG. 6.)

6) Solubility:
Soluble: pyridine, trifluoroacetic acid,
Sparingly soluble: water, dimethyl sulfoxide, methanol 7) Color reaction:
Positive: anisaldehyde-sulphuric acid, HBr-ninhydrine, iodine vapor, molybdophosphoric acid, vanillin-sulphuric acid, Rydon-Smith reagent
Negative: Bromocresol green, ferric chloride, 2,4-dinitrophenyl-hydrazine-sulphuric acid, Sakaguchi reagent, silver nitrate 8) Thin-layer chromatography (TLC)

| Carrier | Solvent system | Rf |
|---|---|---|
| silica gel F$_{254}$*[1] | n-butanol:acetic acid:water (3:1:1) | 0.49 |

*[1]E. Merck AG., Germany

9) High Performance Liquid Chromatography (HPLC)
Carrier: >MCIgel<, a reversed phase silicagel C$_{18}$ column for HPLC manufacture by Mitsubishi Kasei Co. Mobile phase: acetonitrile: 10 mM Sodium hydrogen phosphate buffer (pH 3.4 ) solvent gradient
Flow rate: 1.2 ml/min. Rt=22.4±0.5 min 10) Classification of substance: amphoteric substance 11) Amino acid analysis: Caledothricin B was heated at 120° C. in 6N HCl for 24 hours, followed by subjecting to amino acid analysis to detect tyrosine, threonine×2, glutamine, glycine, histidine.

Caledothricin C:

1) Appearance: white solid
2) Molecular weight (FAB-MS method)
Positive ion mode: m/z 1239 (M+H)$^+$
Negative ion mode: m/z 1237 (M−H)$^−$
3) Molecular formula: $C_{59}H_{90}N_{12}O_{17}$
4) IR spectrum: in KBr tablet (See FIG. 7)

Main absorption wavenumbers (cm$^{-1}$) are as follows: 3368, 2926, 2855, 1671, 1671, 1518, 1204, 1138

Figure 8:
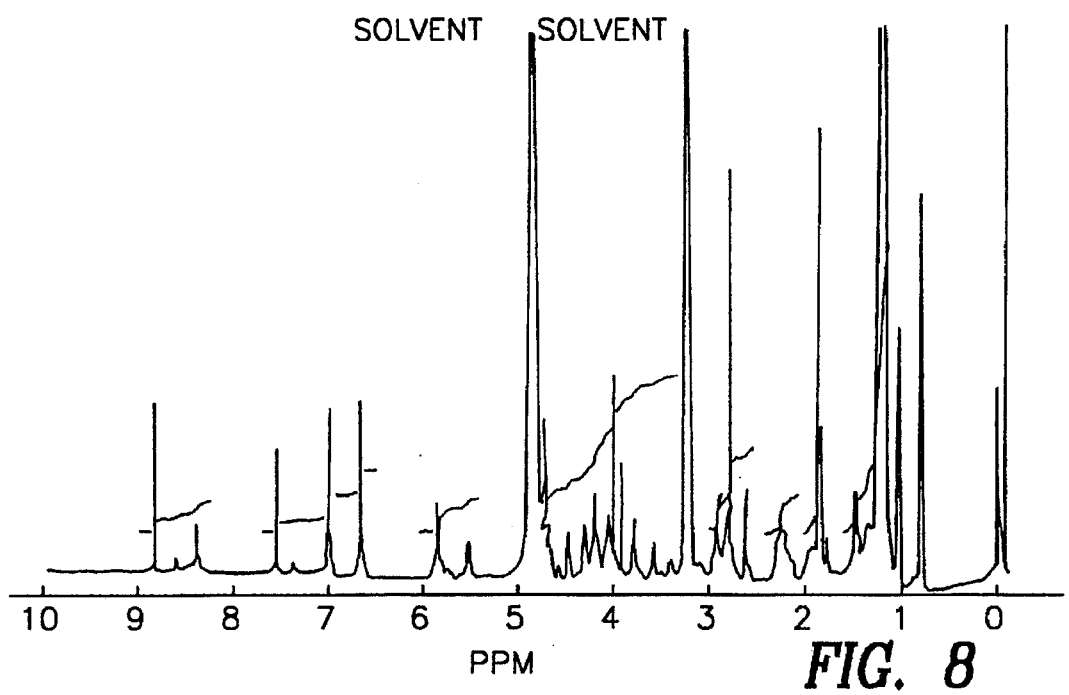
FIG. 8 shows the $^1$H-NMR spectra of caledothricin C.

5) $^1$H-NMR spectrum: 400 MHz, in mixture of dimethylsulfoxide-d$_6$ and trifluoroacetic acid (25:1), (See FIG. 8.)

6) Solubility:
Soluble: pyridine, trifluoroacetic acid,
Sparingly soluble: water, dimethyl sulfoxide, methanol 7) Color reaction:
Positive: anisaldehyde-sulphuric acid, HBr-ninhydrine, iodine vapor, molybdophosphoric acid, vanillin-sulphuric acid, Rydon-Smith reagent
Negative: bromocresol green, ferric chloride, 2,4-dinitrophenyl-hydrazine-sulphuric acid, Sakaguchi reagent, silver nitrate 8) Thin-layer chromatography (TLC)

| Carrier | Solvent system | Rf |
|---|---|---|
| silica gel F$_{254}$*[1] | n-butanol:acetic acid:water (3:1:1) | 0.46 |

*[1]E. Merck AG., Germany

9) High Performance liquid chromatography (HPLC)
Carrier: >MCIgel<, manufactured by Mitsubishi Kasei Co. Mobile phase: acetonitrile: 10 mM sodium hydrogen phosphate buffer (pH 3.4) solvent gradient
Flow rate: 1.2 ml/min. Rt=22.2±0.5 min 10) Classification of substance: amphoteric substance 11) Amino acid analysis: Caledothricin C was heated at 120° C. in 6N HCl for 24 hours, followed by subjecting to amino acid analysis to detect tyrosine, threonine×2, glutamine, glycine, histidine.

Caledothricin D:

1) Appearance: white solid
2) Molecular weight (FAB-MS method):
Positive ion mode: m/z 1355 (M+H)$^+$
Negative ion mode: m/z 1353 (M−H)$^−$
3) Molecular formula: $C_{64}H_{98}N_{12}O_{20}$
4) IR spectrum: in KBr tablet (See FIG. 9)

Main absorption wavenumbers (cm$^{-1}$) are as follows: 3342, 2910, 2830, 1740, 1655, 1527, 1204, 1140

Figure 10:
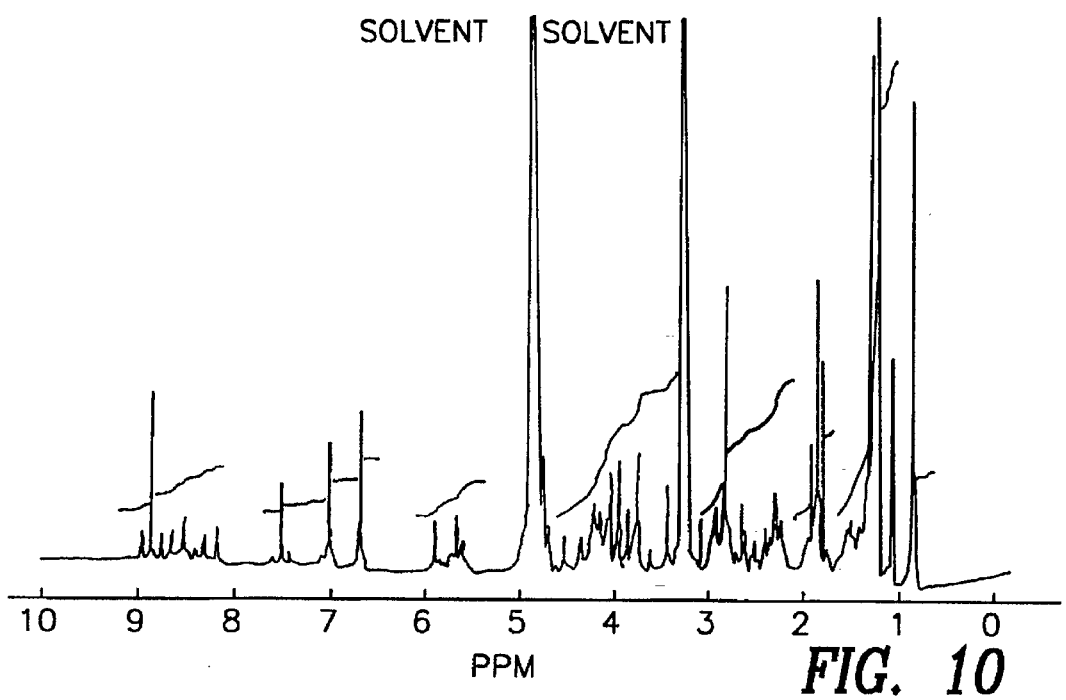
FIG. 10 shows the $^1$H-NMR spectra of caledothricin D.

5) $^1$H-NMR spectrum: 400 MHz, in mixture of dimethylsulfoxide-d$_6$ and trifluoroacetic acid (25:1), (See FIG. 10.)

6) Solubility:
Soluble: pyridine, trifluoroacetic acid,
Sparingly soluble: water, dimethyl sulfoxide, methanol 7) Color reaction:
Positive: anisaldehyde-sulphuric acid, HBr-ninhydrine, iodine vapor, molybdophosphoric acid, vanillin-sulphuric acid, Rydon-Smith reagent
Negative: bromocresol green, ferric chloride, 2,4-dinitrophenyl-hydrazine-sulphuric acid, Sakaguchi reagent, silver nitrate 8) Thin-layer chromatography (TLC)

| Carrier | Solvent system | Rf |
|---|---|---|
| silica gel F$_{254}$*[1] | n-butanol:acetic acid:water (3:1:1) | 0.43 |

*[1]E. Merck AG., Germany

9) High Performance Liquid Chromatography (HPLC)
Carrier: >MCIgel<, manufactured by Mitsubishi Kasei Co.
Mobile phase: acetonitrile: 10 mM sodium hydrogen phosphate buffer (pH 3.4 ) solvent gradient
Flow rate: 1.2 ml/min. Rt=18.2±0.5 min 10) Classification of substance: amphoteric substance 11) Amino acid analysis: Caledothricin D was heated at 120° C. in 6N HCl for 24 hours, followed by subjecting to amino acid analysis to detect tyrosine, threonine×2, glutamine, glycine, histidine.

Caledothricin E:

1) Appearance: white solid

2) Molecular weight (FAB-MS method)

Positive ion mode: m/z 1371 (M+H)$^+$

Negative ion mode: m/z 1369 (M−H)$^−$,

3) Molecular formula: $C_{64}H_{98}N_{12}O_{21}$

Figure 11:
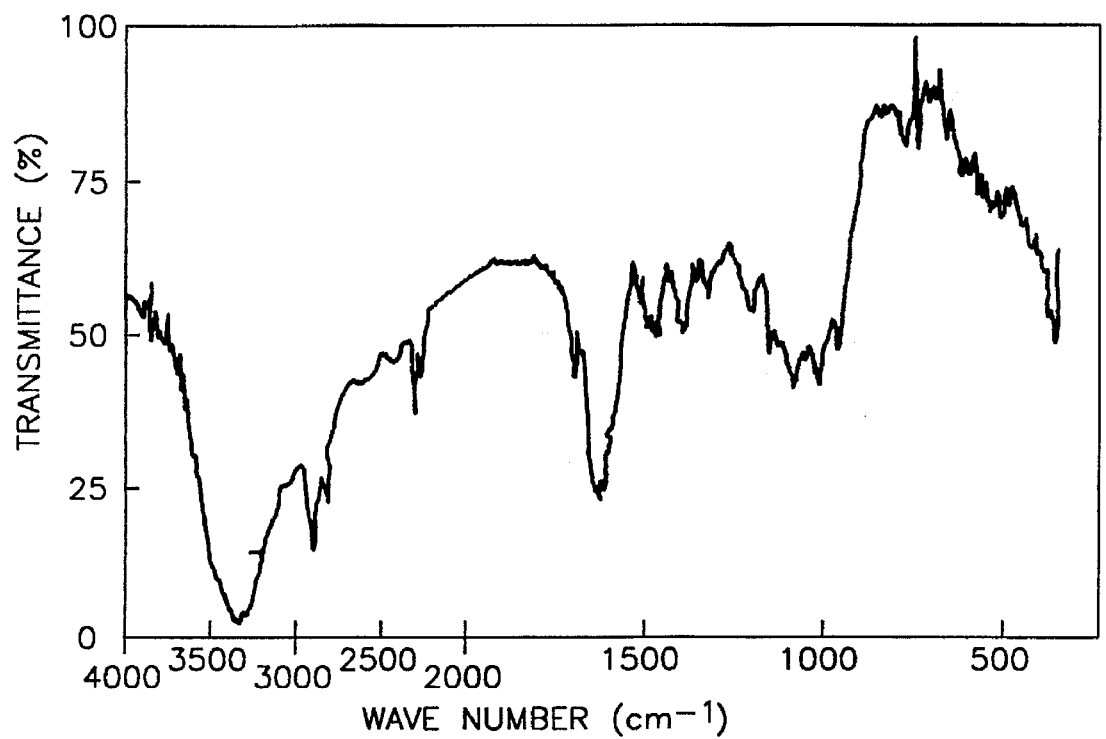
FIG. 11 shows the IR spectra of caledothricin E.

4) IR spectrum: in KBr tablet (See FIG. 11)

Figure 12:
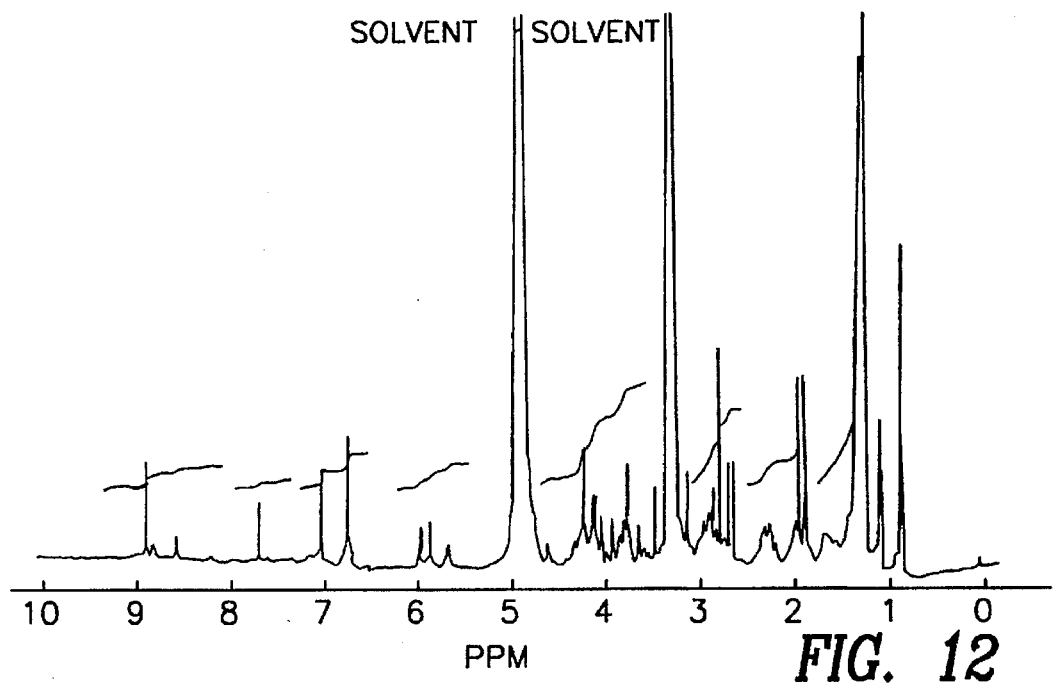
FIG. 12 shows the $^1$H-NMR spectra of caledothricin E.

Main absorption wavenumbers (cm$^{-1}$) are as follows: 3354, 2920, 2850, 1740, 1678, 1530, 1262, 1150–1050, 5) $^1$H-NMR spectrum: 400 MHz, in mixture of dimethylsulfoxide-d$_6$ and trifluoroacetic acid (25:1), (See FIG. 12.)

6) Solubility:

Soluble: pyridine, trifluoroacetic acid,

Sparingly soluble: water, dimethyl sulfoxide, methanol

7) Color reaction:

Positive: anisaldehyde-sulphuric acid, HBr-ninhydrine, iodine vapor, molybdophosphoric acid, vanillin-sulphuric acid, Rydon-Smith reagent Negative: Bromocresol green, Ferric chloride, 2,4-dinitrophenyl-hydrazine-sulphuric acid, Sakaguchi reagent, silver nitrate 8) Thin-layer chromatography (TLC)

| Carrier | Solvent system | Rf |
|---|---|---|
| silica gel F$_{254}$*$^1$ | n-butanol:acetic acid:water (3:1:1) | 0.39 |

*$^1$E. Merck AG., Germany

9) High Performance Liquid Chromatography (HPLC)

Carrier: >MCIgel<, manufactured by Mitsubishi Kasei Co.

Mobile phase: Acetonitrile: 10 mM Sodium hydrogen phosphate buffer (pH 3.4 ) solvent gradient Flow rate: 1.2 ml/min. Rt=17.6±0.5 min 10) Classification of substance: amphoteric substance 11) Amino acid analysis: Caledothricin E was heated at 120° C. in 6N HCl for 24 hours, followed by subjecting to amino acid analysis to detect tyrosine, threonine×2, glutamine, glycine, histidine.

Caledothricin F:

1) Appearance: white solid

2) Molecular weight (FAB-MS method)

Positive ion mode: m/z 1517 (M+H)$^+$

Negative ion mode: m/z 1515 (M−H)$^−$,

3) Molecular formula: $C_{70}H_{108}N_{12}O_{25}$

Figure 13:
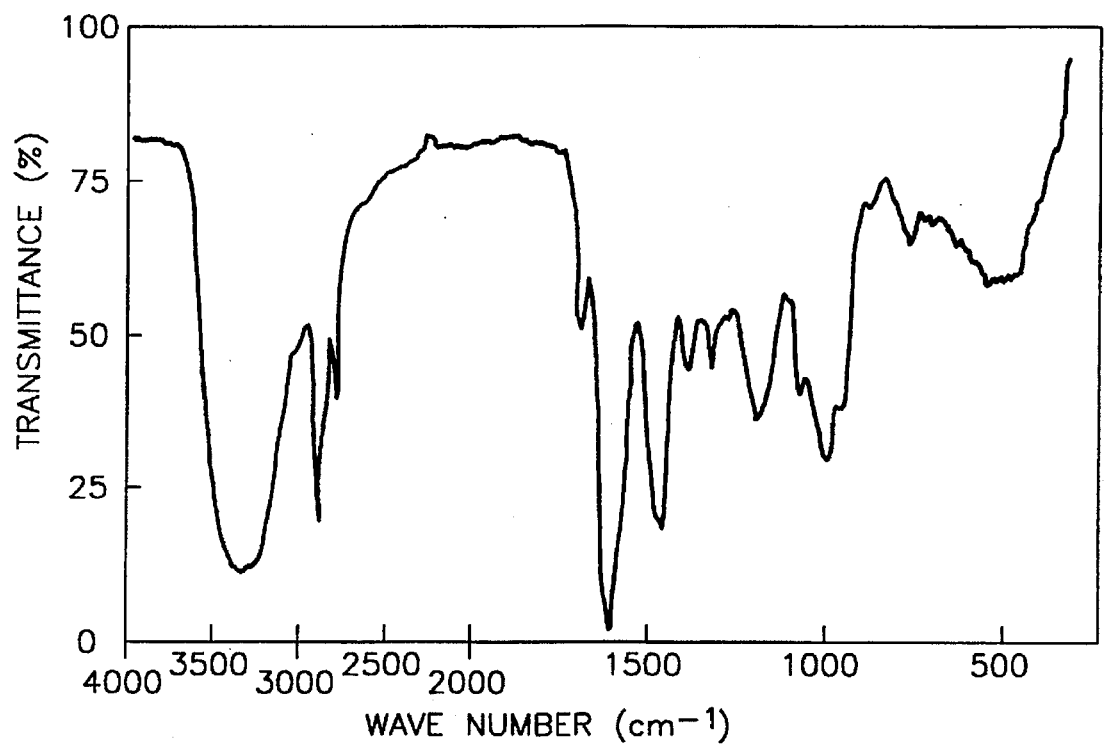
FIG. 13 shows the IR spectra of caledothricin F.

4) IR spectrum: in KBr tablet (See FIG. 13)

Figure 14:
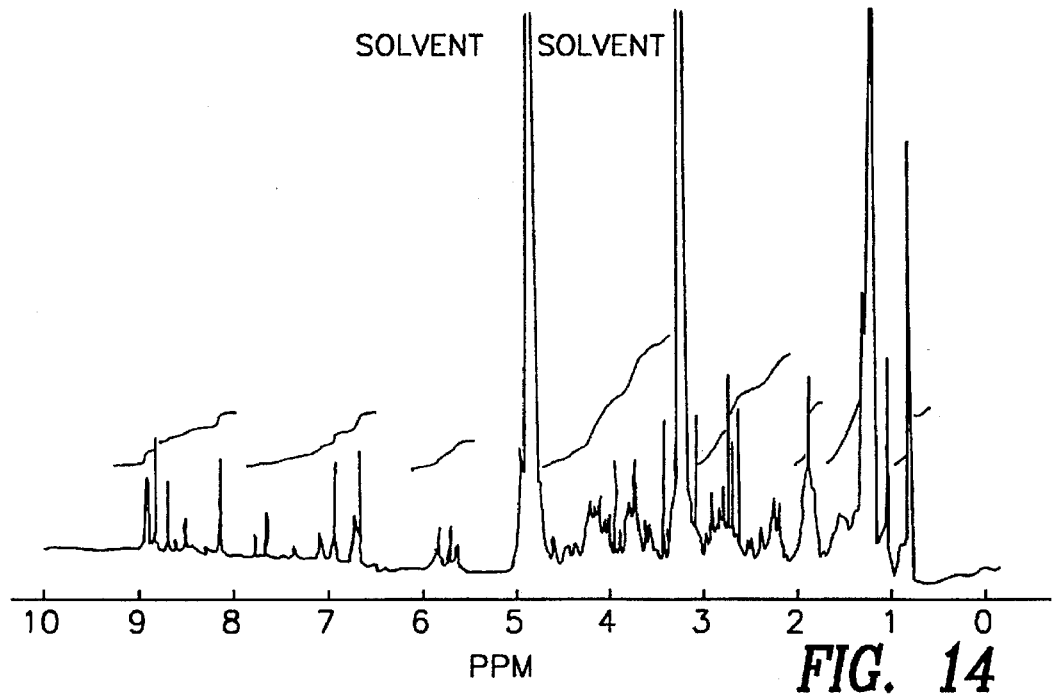
FIG. 14 shows the $^1$H-NMR spectra of caledothricin F.

Main absorption wavenumbers (cm$^{-1}$) are as follows: 3356, 2926, 2855, 1740, 1657, 1518, 1260, 1100–1000, 5) $^1$H-NMR spectrum: 400 MHz, in mixture of dimethylsulfoxide-d$_6$ and trifluoroacetic acid (25:1) (See FIG. 14.)

6) Solubility:

Soluble: pyridine, trifluoroacetic acid,

Sparingly soluble: water, dimethyl sulfoxide, methanol

7) Color reaction:

Positive: anisaldehyde-sulphuric acid, HBr-ninhydrine, iodine vapor, molybdophosphoric acid, vanillin-sulphuric acid, Rydon-Smith reagent Negative: Bromocresol green, ferric chloride, 2,4-dinitrophenyl-hydrazine-sulphuric acid, Sakaguchi reagent, silver nitrate 8) Thin-layer chromatography (TLC)

| Carrier | Solvent system | Rf |
|---|---|---|
| silica gel F$_{254}$*$^1$ | n-butanol:acetic acid:water (3:1:1) | 0.18 |

*$^1$E. Merck AG., Germany

9) High Performance Liquid Chromatography (HPLC)

Carrier: >MCIgel<, manufactured by Mitsubishi Kasei Co.

Mobile phase: Acetonitrile: 10 mM Sodium hydrogen phosphate buffer (pH 3.4 ) solvent gradient Flow rate: 1.2 ml/min. Rt=16.3±0.5 min 10) Classification of substance: amphoteric substance 11) Amino acid analysis: Caledothricin A was heated at 120° C. in 6N HCl for 24 hours, followed by subjecting to amino acid analysis to detect tyrosine, threonine×2, glutamine, glycine, histidine.

Caledothricin G:

1) Appearance: white solid

2) Molecular weight (FAB-MS method)

Positive ion mode: m/z 1373 (M+H)$^+$

3) Molecular formula: $C_{63}H_{96}N_{12}O_{22}$

Figure 15:
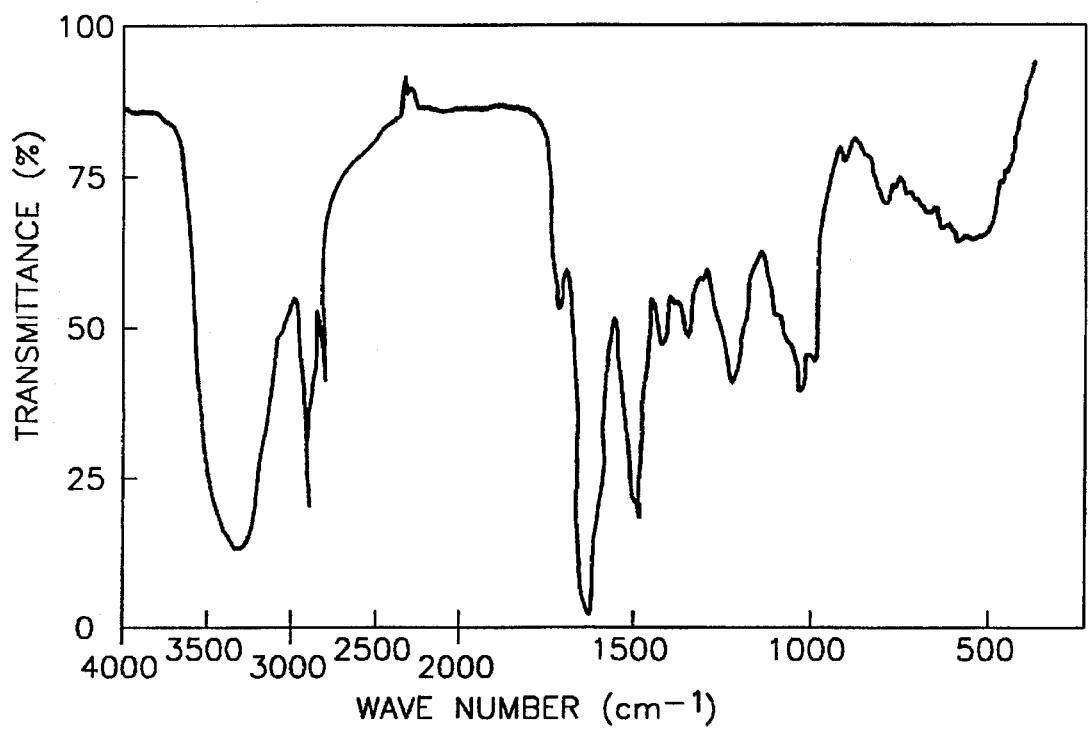
FIG. 15 shows the IR spectra of caledothricin G.

4) IR spectrum: in KBr tablet (See FIG. 15)

Main absorption wavenumbers (cm$^{-1}$) are as follows: 3350, 2926, 2855, 1739, 1659, 1518, 1265, 1120–1030, 5) $^1$H-NMR spectrum: 400 MHz, in mixture of dimethylsulfoxide-d$_6$ and trifluoroacetic acid (25:1), (See FIG. 16.)

6) Solubility:

Soluble: pyridine, trifluoroacetic acid,

Sparingly soluble: water, dimethyl sulfoxide, methanol

7) Color reaction:

Positive: anisaldehyde-sulphuric acid, HBr-ninhydrine, iodine vapor, molybdophosphoric acid, vanillin-sulphuric acid, Rydon-Smith reagent Negative: Bromocresol green, ferric chloride, 2,4-dinitrophenyl-hydrazine-sulphuric acid, Sakaguchi reagent, silver nitrate 8) Thin-layer chromatography (TLC)

| Carrier | Solvent system | Rf |
|---|---|---|
| silica gel F$_{254}$*$^1$ | n-butanol:acetic acid:water (3:1:1) | 0.24 |

*$^1$E. Merck AG., Germany

9) High Performance Liquid Chromatography (HPLC)

Carrier: >MCIgel<, manufactured by Mitsubishi Kasei Co.

Mobile phase: Acetonitrile: 10 mM Sodium hydrogen phosphate buffer (pH 3.4 ) solvent gradient 5 Flow rate: 1.2 ml/min. Rt=15.6±0.5 min 10) Classification of substance: amphoteric substance 11) Amino acid analysis: Caledothricin G was heated at 120° C. in 6N HCl for 24 hours, followed by subjecting to amino acid analysis to detect tyrosine, threonine×2, glutamine, glycine, histidine.

Caledothricin H:
1) Appearance: white solid
2) Molecular weight (FAB-MS method)
Positive ion mode: m/z 1343 (M+H)$^+$
Negative ion mode: m/z 1341 (M−H)$^−$,
3) Molecular formula: $C_{62}H_{94}N_{12}O_{21}$
4) IR spectrum: in KBr tablet (See FIG. 17)

Main absorption wavenumbers (cm$^{-1}$) are as follows: 3386, 2925, 2850, 1745, 1670, 1520, 1210, 1140

Figure 18:
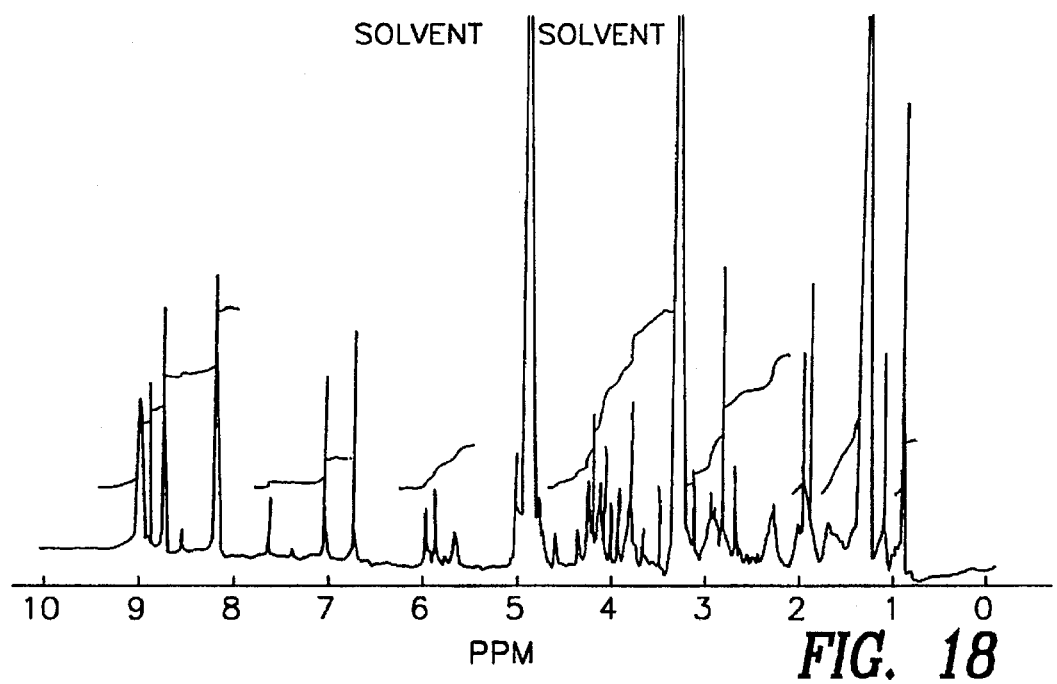
FIG. 18 shows the $^1$H-NMR spectra of caledothricin H.

5) $^1$H-NMR spectrum: 400 MHz, in mixture of dimethylsulfoxide-d$_6$ and trifluoroacetic acid (25:1), (See FIG. 18.)

6) Solubility:
Soluble: pyridine, trifluoroacetic acid,
Sparingly soluble: water, dimethyl sulfoxide, methanol 7) Color reaction:
Positive: anisaldehyde-sulphuric acid, HBr-ninhydrine, iodine vapor, molybdophosphoric acid, vanillin-sulphuric acid, Rydon-Smith reagent Negative: bromocresol green, ferric chloride, 2,4-dinitrophenyl-hydrazine-sulphuric acid, Sakaguchi reagent, silver nitrate 8) Thin-layer chromatography (TLC)

| Carrier | Solvent system | Rf |
|---|---|---|
| silica gel F$_{254}$*$^1$ | n-butanol:acetic acid:water (3:1:1) | 0.22 |

*$^1$E. Merck AG., Germany

9) High Performance Liquid Chromatography (HPLC)
Carrier: >MCIgel<, manufactured by Mitsubishi Kasei Co.
Mobile phase: Acetonitrile: 10 mM Sodium hydrogen phosphate buffer (pH 3.4) solvent gradient
Flow rate: 1.2 ml/min. Rt=12.3±0.5 min 10) Classification of substance: amphoteric substance 11) Amino acid analysis: Caledothricin H was heated at 120° C. in 6N HCl for 24 hours, followed by subjecting to amino acid analysis to detect tyrosine, threonine×2, glutamine, glycine, histidine.

Caledothricin I:
1) Appearance: white solid
2) Molecular weight (FAB-MS method)
Positive ion mode: m/z 1327 (M+H)$^+$
Negative ion mode: m/z 1325 (M−H)$^−$
3) Molecular formula: $C_{62}H_{94}N_{12}O_{20}$
4) IR spectrum: in KBr tablet (See FIG. 19)

Main absorption wavenumbers (cm$^{-1}$) are as follows: 3347, 2920, 2850, 1679, 1540, 1205, 1140

Figure 20:
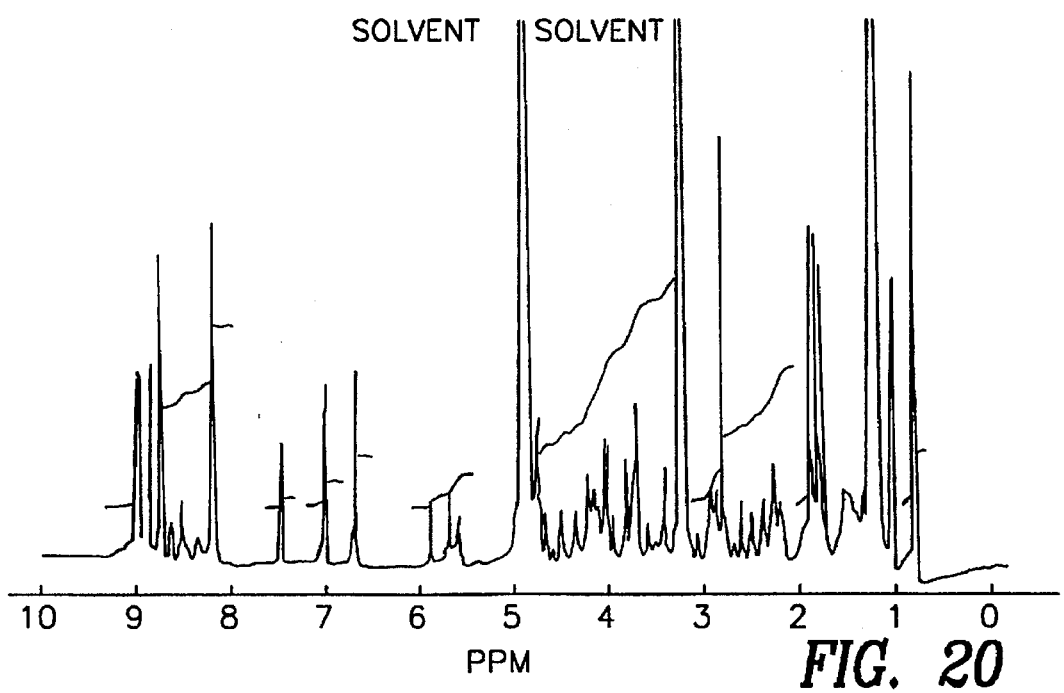
FIG. 20 shows the $^1$H-NMR spectra of caledothricin I.

5) $^1$H-NMR spectrum: 400 MHz, in mixture of dimethylsulfoxide-d$_6$ and trifluoroacetic acid (25:1), (See FIG. 20.)

6) Solubility:
Soluble: pyridine, trifluoroacetic acid,
Sparingly soluble: water, dimethyl sulfoxide, methanol 7) Color reaction:
Positive: anisaldehyde-sulphuric acid, HBr-ninhydrine, iodine vapor, molybdophosphoric acid, vanillin-sulphuric acid, Rydon-Smith reagent Negative: bromocresol green, ferric chloride, 2,4-dinitrophenyl-hydrazine-sulphuric acid, Sakaguchi reagent, silver nitrate 8) Thin-layer chromatography (TLC)

| Carrier | Solvent system | Rf |
|---|---|---|
| silica gel F$_{254}$*$^1$ | n-butanol:acetic acid:water (3:1:1) | 0.43 |

*$^1$E. Merck AG., Germany

9) High Performance Liquid Chromatography (HPLC)
Carrier: >MCIgel<, manufactured by Mitsubishi Kasei Co.
Mobile phase: Acetonitrile: 10 mM Sodium hydrogen phosphate buffer (pH 3.4) solvent gradient
Flow rate: 1.2 ml/min. Rt=12.6±0.5 min 10) Classification of substance: amphoteric substance 11) Amino acid analysis: Caledothricin I was heated at 120° C. in 6N HCl for 24 hours, followed by subjecting to amino acid analysis to detect tyrosine, threonine×2, glutamine, glycine, histidine.

Caledothricins A, B, C, D, E, F, G, H, and I showed quite similar $^1$H-NMR spectra as shown in FIGS. 3, 6, 8, 10, 12, 14, 16, 18 and 20 and IR spectra as shown in FIGS. 2, 5, 7, 9, 11, 13, 15 17 and 19, respectively indicating that the caledothricins are depsipeptide homologues. Amino acid analysis of the caledothricins revealed that they had the same amino acid residues, which are threonine, glycine, glutamine, histidine and tyrosine. The presence of fatty acid units was indicated by their $^1$H-NMR spectra (a signal at 0.95 ppm assignable to a methyl group and signals at 1.2–1.4 ppm assignable to methylene groups).

Caledothricins A, B, C, D, E, F, G, H and I are prepared by cultivating a microorganism belonging to the genus Pseudomonas under aerobic conditions in an aqueous culture medium, and isolating the caledothricins.

The microorganisms used in the present invention includes all strains belonging to the genus Pseudomonas, which are capable of producing caledothricins, A, B, C, D, E, F, G, H and I. The microorganisms used in the present invention may also be functional equivalents subcultures, mutants and variants of strains belonging to the genus Psuedomones which are capable of providing caledothricins A, B, C, D, E, F, G, H, and I, which functional equivalents, subcultures, mutants and variants are also capable of producing caledothricins A, B, C, D, E, F, G, H, and I.

Preferred strains are Pseudomonas spp. BA 7399 and BA 8429 which were isolated from a soil sample. The strains Pseudomonas spp. BA 7399 and BA 8429 have been deposited on Aug. 2, 1994, at the National Institute of Bioscience and Human-Technology, Japan, under the Budapest Treaty under the deposit numbers

| | |
|---|---|
| *Pseudomonas sp.* BA7399 | FERM BP-4766 |
| *Pseudomonas sp.* BA8429 | FERM BP-4767 |

The morphological and physiological characteristics of Pseudomonas spp. BA 7399 and BA 8429 follow Strain BA 7399 and BA 8429 were Gram-negative, non-sporulating, rod-shaped, aerobic, and motile with several (more than 6) polar flagella. The color of colonies were pale yellow. The oxidase and catalase production were positive. The OF test of the strain BA 7399 was oxidative, but the strain BA 8429 was negative. Growth Factors were not required. These characteristics indicated that two strains, BA 7399 and BA 8429 belonged to the genus Pseudomonas Migula. Therefore, these strains were identified as Pseudomonas spp. BA 7399 and BA 8429.

The cultivation is carried out in a culture medium which contains customary nutrients usable by the microorganism being cultivated. As carbon sources there are mentioned, for example, glucose, levulose, galactose, mannose, sorbose, arabinose, xylose, sucrose, starch, glycerol, molasses, dextrin and mixtures thereof. Nitrogen sources are, for example, soybean meal, cottonseed meal, corn meal, meat extract, peptone, dried yeast, yeast extract, cornsteep liquor, ammonium sulphate, sodium nitrate and mixtures thereof. Moreover, there may be added to the culture medium other organic or inorganic substances for promoting the growth of the microorganism and for increasing the production of caledothricins, examples of such substances being inorganic salts, for example, calcium carbohydrate, sodium chloride, sodium thiosulphate, phosphates and the like.

The cultivation is carried out under aerobic conditions in an aqueous medium, preferably by submerged fermentation. The cultivation is preferably carried out at a temperature of about 20° C.–35° C., the optimal temperature being 27° C. The cultivation is preferably carried out at a pH of about 3 to 9. The cultivation time depends on the conditions under which the cultivation is carried out. In general, cultivation is carried at 24° C. for 200 hours.

For harvesting the caledothricins from their culture medium, separation methods which are usually employed to isolate metabolites produced by microbes from their culture medium are properly used. For example, caledothricin A, a n-butanol extractable amphoteric substance, is contained mainly in mycelial cake. It is recovered by subjecting the culture medium to filtration or centrifugation to collect cells, and extracting the resulting mycelial cake with an appropriate solvent to recover the desired products. The solvents which can be used for the extraction include water-soluble organic solvents or hydrous solutions of water-soluble organic solvents, such as methanol, ethanol, acetone, hydrous acetone, and hydrous alcohols.

Salts, water soluble substances, and the like can be removed from the resulting extract by partition between water and water-immiscible organic solvents, such as n-butanol, methyl ethylketone, and the like. For removing from the extract coloring substances, fat-soluble substance, or the like there can be used silica gel, molecular sieve type resins such as >SEPHADEX< (Pharmacia, Sweden) a cross-linked dextran gel and >TOYOPEARL< (Toyo Soda Manufacturing Co., Japan), a hydrophilic vinyl polymer gel and the like.

For further purification of the compounds high performance liquid chromatography (HPLC) is advantageously used. Carriers which can be used in such HPLC include reverse phase type resin such as YMC gel (Yamamura Chemical Laboratories, Japan), or >CAPCEL PAK< gel (Shiseido, Co. Ltd., Japan) a polymer coated reversed phase silica gel $C_{18}$ column for HPLC. As the mobile phase, solvent system consisting a mixture of aqueous buffer solution and appropriate water-soluble organic solvent such as methanol acetonitrile, and the like are used.

The eluate fraction thus purified and fractioned is subjected to concentration, freeze-drying or crystallization to pulverize or crystallize caledothricins.

Pharmacologically acceptable salts (for example, potassium salt, calcium salt and hydrochloric acid salt and hydrochloric acid salt and the like) are prepared from caledothricins (free form) by conventional methods can be employed.

In vitro Antifungal Activity

Minimal inhibitory concentrations (MICs) of caledothricins A, B, C, D, E, F, G, H and I against representative pathogenic fungi are shown in Table 1. MIC is defined as the minimal concentration of test compound at which no visible growth is detected. Culture media employed for measuring MICs were yeast nitrogen base (Difco) supplemented with 1% of glucose, 0.2% of low melting point agarose and 0.25% of $K_2HPO_4$ (pH 7.0). The low melting point agarose was omitted when antifungal activity against *Candida albicans* and *Cryptococcus neoformans* was measured. The culture media were inoculated with fungal cells at the final concentration of 10,000 cfu/ml. Plates were incubated for 1–12 days at 27° C. All MIC values in Table 1 are expressed as µg/ml of the test compounds. Fluconazole is a known triazole antifungal agent.

TABLE 1

Antifungal activity of caledothricins A–I

| STRAINS | MIC (µg/ml) | | | | | | | | | |
|---|---|---|---|---|---|---|---|---|---|---|
|  | A | B | C | D | E | F | G | H | I | FCZ* |
| *Candida albicans* | | | | | | | | | | |
| 652 | 0.78 | 0.78 | 0.78 | 1.56 | 6.25 | 6.25 | 0.39 | 0.78 | 0.78 | >200 |
| C42 | 1.56 | 1.56 | 0.78 | 1.56 | 3.13 | 6.25 | 0.39 | 3.13 | 3.13 | >200 |
| ATCC48130 | 0.78 | 0.78 | 0.78 | 0.78 | 1.56 | 6.25 | 0.39 | 1.56 | 0.78 | >200 |
| KB | 0.2 | 0.2 | 0.2 | 0.2 | 0.39 | 0.78 | 0.2 | 0.39 | 0.39 | >200 |
| AD | 0.2 | 0.39 | 0.2 | 0.2 | 0.39 | 1.56 | 0.2 | 0.39 | 0.39 | 200 |
| *Cryptococcus neoformans* | | | | | | | | | | |
| MTU13001 | 0.2 | 0.2 | 0.2 | 0.2 | 0.39 | 0.78 | 0.2 | 0.39 | 0.2 | 12.5 |
| 422 | 0.2 | 0.2 | 0.2 | 0.2 | 0.2 | 0.39 | 0.2 | 0.2 | 0.2 | >200 |
| *Aspergillus fumigatus* | | | | | | | | | | |
| MTU06002 | 0.16 | 0.31 | 1.25 | 1.25 | 2.5 | 0.63 | 0.16 | 1.25 | 1.25 | >200 |
| CF1004 | 0.16 | 0.16 | 1.25 | 1.25 | 1.25 | 0.63 | 0.16 | 1.25 | 1.25 | >200 |

TABLE 1-continued

Antifungal activity of caledothricins A–I

| STRAINS | MIC (µg/ml) | | | | | | | | | |
|---|---|---|---|---|---|---|---|---|---|---|
| | A | B | C | D | E | F | G | H | I | FCZ* |
| 437<br>*Absidia corymbifera* | 0.31 | 0.31 | 2.5 | 5 | 2.5 | 2.5 | 0.63 | 2.5 | 2.5 | >200 |
| IFO8084<br>*Trichosporon beigelii* | 0.39 | 0.2 | 0.2 | NT | NT | NT | NT | NT | 0.2 | >200 |
| ATCC 28592<br>*Trichophyton mentagrophytes* | 0.2 | 0.2 | 0.1 | NT | NT | NT | NT | NT | 0.2 | 0.39 |
| CF1007 | 0.05 | 0.025 | 0.05 | NT | NT | NT | NT | NT | 0.39 | >200 |

*fluconazole
NT; not tested

Caledothricins A, B, C, D, E, F, G, H and I show potent antifungal activity with wide spectra. They inhibited growth of all three representative pathogenic fungi, *Candida albicans*, *Cryptococcus neoformans* and *Aspergillus fumigatus*. In addition, potent inhibition against filamentous fungi was also observed as shown in Table 1. Acute toxicity of caledothricins A to I was not observed.

For the therapeutic use, caledothricins can be prepared into pharmaceutical compositions of various forms in accordance with known techniques. Pharmaceutical compositions of the invention comprise an effective amount of at least one of caledothricin A, B, C, D, E, F, G, H, or I, or salts thereof, and an inert carrier.

For the treatment of candidiasis, the caledothricins of the invention preferably, caledothricin A, can be administrated intravenously, subcutaneously or intramuscularly, as a solution in physiological saline, usually at a dose of 0.1 to 50 mg/kg/day, preferably 0.5 to 20 mg/kg/day. For oral administration, the caledothricins of the invention, preferably, caledothricin A, preferably are formulated as capsules or sugar-coated tablets by conventional processes and administrated at a dose of usually 0.1 to 100 mg/kg/day, preferably 1 to 50 mg/kg/day.

The caledothricins of the invention can also be used as a disinfectant for topical use. For example the caledothricins of the invention, preferably, caledothricin A, can be used for sterilization and disinfection of the skin or mucous membrane of human and animals by applying it as a liquid composition prepared by dissolving the caledothricin in, for example, distilled water at a concentration of usually 0.1 to 10 (wt./Vol.) %, preferably 0.5 to 5 (wt./vol.) % or an ointment using vaseline or lanolin as a base, containing usually 0.2 to 100 mg, preferably 1 to 20 mg of caledothricin per gram.

The following Examples further illustrate the present invention. The percentages given are by weight/volume.

EXAMPLE 1

The cell suspension from well grown slant of Pseudomonas sp. BA 7399 was inoculated into a 500 ml Erlenmeyer flask containing 100 ml of a medium consisting of dextrin 3%, >AJIPRONE<E3 (Ajinomoto) (soybean extract) 1.5%, >POLYPEPTON< (Wako) (milk casein) 0.2%, corn gluten meal (Shouwasangyou) 1.5%, Na2S2O3 0.1% and disfoam 1 drop/flask (nissan). The flask was shaken at 220 rpm for 1 day at 27° C. Fifty 0.2 ml aliquots of the resultant culture were each transferred to individual 500-ml flasks containing the above medium. The fermentation was conducted on a rotary shaker at 220 rpm at 27° C. After 2 days cultivation, the resultant culture broth was subjected to the isolation procedure described below.

The cultured broth (5 L) thus obtained was subjected to continuous centrifugation to obtain mycelial cake. The mycelial cake was added to ethanol (1.3 L) and the mixture was stirred. The mixture was filtered and the ethanol extract (1.4 L) concentrated to dryness under reduced pressure. The residue (6.4 g) was dissolved in water (2 L) and the suspension thus obtained was adjusted to pH 2. n-Butanol (2 L) was added and the mixture was stirred, followed by removal of the water layer. Water (2 L) was added to the organic layer thus obtained and the mixture was adjusted to pH 9. The mixture was stirred followed by removal of the water layer. The organic layer thus obtained was concentrated to dryness under reduced pressure, and the residue (4.5 g) was then subjected to column chromatography on silica gel (1 L). The column was first eluted with a mixture of dichloromethane and methanol (1:1). Thereafter, the antibiotics were eluted with a mixture of dichloromethane and methanol (1:1) and then methanol. Fractions containing the antibiotics were combined and concentrated to dryness under reduced pressure. The residue (1.4 g) thus obtained was subjected to column chromatography on >SEPHADEX<LH20 (1.5 L). Elution was carried out with methanol. Fractions containing the antibiotics were combined (205 ml) and then concentrated to dryness under reduced pressure. The crude antibiotics dissolved in pyridine were subjected to high performance liquid chromatography (HPLC) on a YMCpack $C_{18}$ column (20 mmfx250 mm), eluting with a solvent system of acetonitrile: 10 mM sodium hydrogen phosphate buffer (pH 3.4) (45:55) for fractionation. The fractions containing the individual caledothricins A to I were combined followed by concentration. n-Butanol (30 ml) was added to the concentrate (30 ml) stirred for 5 min followed by removal of the water layer. The organic layer thus obtained was washed with water (15 ml×2) and concentrated to dryness under reduced pressure. The residue was dissolved in pyridine and concentrated to dryness under reduced pressure again to obtain white powdery caledothricin A (30 mg), B (7.8 mg), C (3.7 mg), D (2.1 mg), E (1.0 mg), F (1.4 mg), G (1.1 mg), H (1.6 mg) and I (3.0 mg).

EXAMPLE 2

In a manner analogous to that described in Example 1 except that Pseudomonas sp. BA 8429 was used in place of Pseudomonas sp. BA 7399, there were obtained white powdery caledothricins A (12.5 mg), B (2.6 mg), C (trace), D (trace), E (trace), F (0.3 mg), G (5.6 mg), H (trace) and I (3.2 mg).

EXAMPLE 3

Injectable solutions each containing the following ingredients were manufactured in a conventional manner:

| | |
|---|---|
| Caledothricin A | 20 mg |
| di-Sodium hydrogenphosphate, anhydrous | 7.6 mg |
| Sodium diphosphate dehydrate | 2.0 mg |
| Ethyl alcohol | 150 mg |
| Distilled water, deionized, sterile | 850 mg |
| Total | 1029.6 mg |

We claim:

1. Caledothricin A having the following properties:

1) Appearance: white solid
  2) Specific rotation: $[\alpha]^{24}D$ $-50.8°\pm6.4°$ (c=0.10, in pyridine)
  3) Molecular weight (FAB-MS method):
     Positive ion mode: m/z 1401 (M+H)$^+$, 1423 (M+Na)$^+$
     Negative ion mode: m/z 1399 (M–H)$^-$, 1417 (M+H$_2$O–H)$^-$
  4) Molecular formula: $C_{65}H_{100}N_{12}O_{22}$
  5) High resolution mass spectroscopy (for M+H):
     Found: 1401.7117 Calcd. for $C_{65}H_{101}N_{12}O_{22}$:1401.7143
  6) UV spectrum: in methanol (as shown in FIG. 1)
     $\lambda_{max}$ 203±5 (ε4300), 224±5 (ε2900 sh), 275±5 (ε280 sh) (in methanol)
     $\lambda_{max}$ 203±5 (ε3500), 220±5 (ε2900 sh), 275±5 (ε315 sh) (in N/10HCl-methanol)
     $\lambda_{max}$ 204±5 (ε7200), 225±5 (ε2600 sh), 245±5 (ε1600 sh), 295±5 (ε200 sh) (in N/10NaOH-methanol)
  7) IR spectrum: in KBr tablet (as shown in FIG. 2)
     Main absorption wavenumbers (cm$^{-1}$) are as follows:
     3298, 2925, 2854, 1745, 1657, 1517, 1262, 1100–1000
  8) $^1$H-NMR spectrum: 400 MHz, in mixture of dimethylsulfoxide-d$_6$ and trifluoroacetic acid (25:1), (as shown in FIG. 3)
  9) $^{13}$C-NMR spectrum: 100 MHz, in mixture of dimethylsulfoxide-d$_6$ and trifluoroacetic acid (25:1), (as shown in FIG. 4)
  10) Solubility:
     Soluble: pyridine, trifluoroacetic acid,
     Sparingly soluble: water, dimethyl sulfoxide, methanol
  11) Color reaction:
     Positive: anisaldehyde-sulphuric acid, HBr-ninhydrine, iodine vapor, molybdophosphoric acid, vanillin-sulphuric acid, Rydon-Smith reagent
     Negative: bromocresol green, ferric chloride, 2,4-dinitrophenyl-hydrazine-sulphuric acid, Sakaguchi reagent, silver nitrate
  12) Thin-layer chromatography (TLC)

| Carrier | Solvent system | Rf |
|---|---|---|
| silica gel F254 | dichloromethane:methanol:water (60:35:5) | 0.13 |
|  | n-butanol:acetic acid:water (3:1:1) | 0.25 |

13) High performance liquid chromatography (HPLC):
     Carrier: >YMC-PAK<A303
     Mobile phase: acetonitrile: 10 mM sodium hydrogen phosphate buffer (pH 3.4 )=45:55
     Flow rate: 1 ml/min. Rt=16.3±0.5 min
  14) Classification of substance: amphoteric substance
  15) Amino acid analysis: Caledothricin A was heated at 120° C. in 6N HCl for 24 hours, followed by subjecting to amino acid analysis to detect tyrosine, threonine×2, glutamine, glycine, histidine, and its physiologically acceptable salt.

Figure 5:
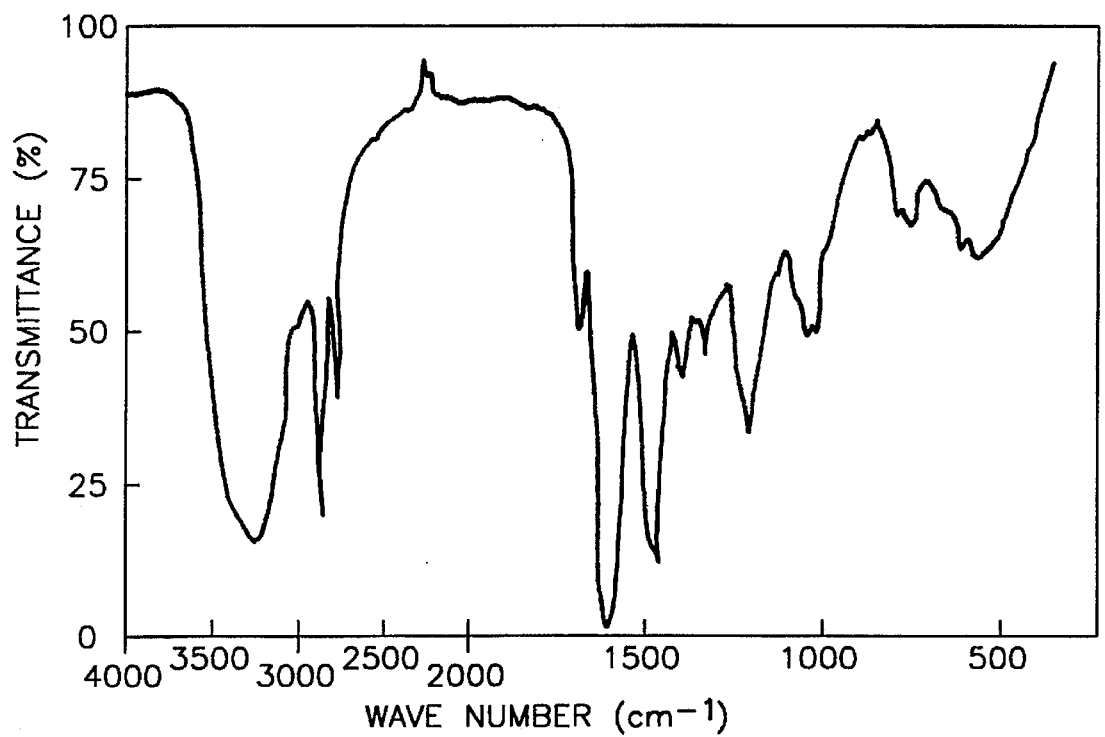
FIG. 5 shows the IR spectra of caledothricin B.

2. Caledothricin B having the following properties:

1) Appearance: white solid
  2) Molecular weight (FAB-MS method)
     Positive ion mode: m/z 1223 (M+H)$^+$
     Negative ion mode: m/z 1221 (M–H)$^-$
  3) Molecular formula: $C_{59}H_{90}N_{12}O_{16}$
  4) IR spectrum: in KBr tablet (as shown in FIG. 5)
     Main absorption wavenumbers (cm$^{-1}$) are as follows:
     3304, 2926, 2854, 1741, 1657, 1518, 1261, 1130–1060,
  5) $^1$H-NMR spectrum: 400 MHz, in mixture of dimethylsulfoxide-d$_6$ and trifluoroacetic acid (25:1), (as shown in FIG. 6.)
  6) Solubility:
     Soluble: pyridine, trifluoroacetic acid,
     Sparingly soluble: water, dimethyl sulfoxide, methanol
  7) Color reaction:
     Positive: anisaldehyde-sulphuric acid, HBr-ninhydrine, iodine vapor, molybdophosphoric acid, vanillin-sulphuric acid, Rydon-Smith reagent
     Negative: bromocresol green, ferric chloride, 2,4-dinitrophenyl-hydrazine-sulphuric acid, Sakaguchi reagent, silver nitrate
  8) Thin-layer chromatography (TLC):

| Carrier | Solvent system | Rf |
|---|---|---|
| silica gel F254 | n-butanol:acetic acid:water (3:1:1) | 0.49 |

9) High performance liquid chromatography (HPLC)
     Carrier: >MCIgel<
     Mobile phase: acetonitrile: 10 mM sodium hydrogen phosphate buffer (pH 3.4 ) solvent gradient
     Flow rate: 1.2 ml/min. Rt=22.4±0.5 min
  10) Classification of substance: amphoteric substance
  11) Amino acid analysis: Caledothricin B was heated at 120° C. in 6N HCl for 24 hours, followed by subjecting to amino acid analysis to detect tyrosine, threonine×2, glutamine, glycine, histidine, and its physiologically acceptable salt.

Figure 7:
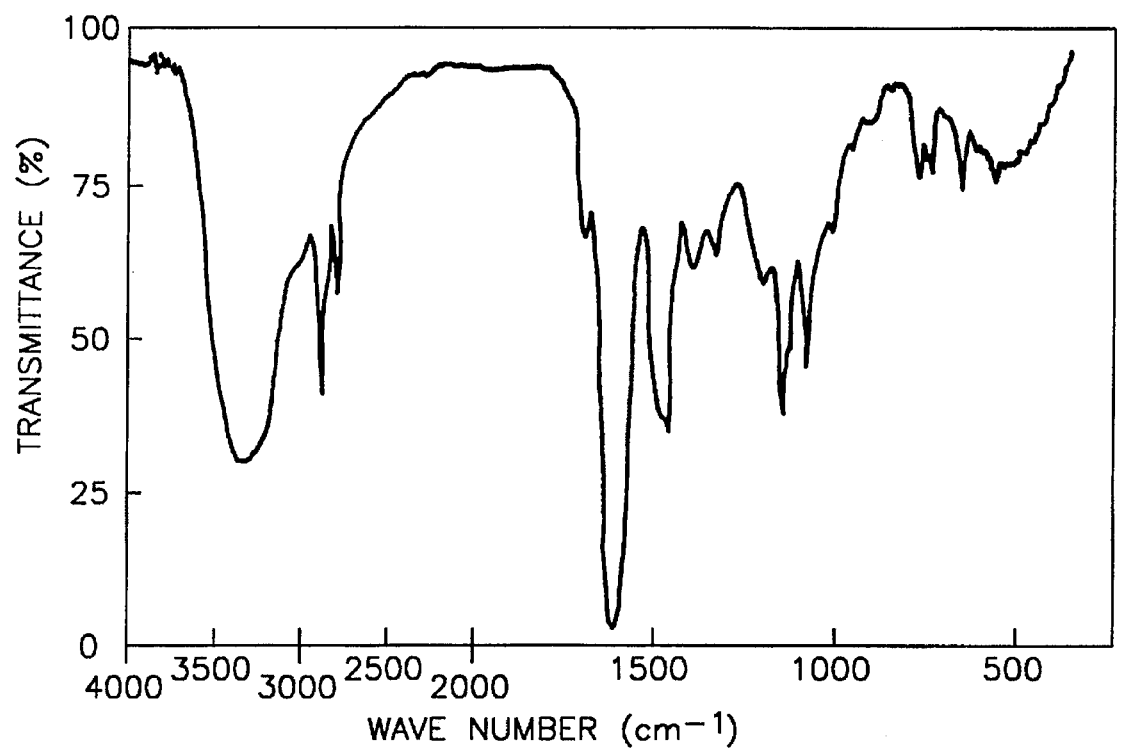
FIG. 7 shows the IR spectra of caledothricin C.

3. Caledothricin C having the following properties:

1) Appearance: white solid
2) Molecular weight (FAB-MS method)
   Positive ion mode: m/z 1239 (M+H)$^+$
   Negative ion mode: m/z 1237 (M−H)$^-$
3) Molecular formula: $C_{59}H_{90}N_{12}O_{17}$
4) IR spectrum: in KBr tablet (as shown in FIG. 7)
   Main absorption wavenumbers (cm$^{-1}$) are as follows:
   3368, 2926, 2855, 1740, 1671, 1518, 1204, 1138
5) $^1$H-NMR spectrum: 400 MHz, in mixture of dimethylsulfoxide-d$_6$ and trifluoroacetic acid (25:1), (as shown in FIG. 8.)
6) Solubility:
   Soluble: pyridine, trifluoroacetic acid,
   Sparingly soluble: water, dimethyl sulfoxide, methanol
7) Color reaction:
   Positive: anisaldehyde-sulphuric acid, HBr-ninhydrine, iodine vapor, molybdophosphoric acid, vanillin-sulphuric acid, Rydon-Smith reagent
   Negative: bromocresol green, ferric chloride, 2,4-dinitrophenyl-hydrazine-sulphuric acid, Sakaguchi reagent, silver nitrate
8) Thin-layer chromatography (TLC)

| Carrier | Solvent system | Rf |
|---|---|---|
| silica gel F254 | n-butanol:acetic acid:water (3:1:1) | 0.46 |

9) High Performance liquid chromatography (HPLC)
   Carrier: >MCIgel<
   Mobile phase: acetonitrile: 10 mM sodium hydrogen phosphate buffer (pH 3.4) solvent gradient
   Flow rate: 1.2 ml/min. Rt=22.2±0.5 min
10) Classification of substance: amphoteric substance
11) Amino acid analysis: Caledothricin C was heated at 120° C. in 6N HCl for 24 hours, followed by subjecting to amino acid analysis to detect tyrosine, threonine×2, glutamine, glycine, histidine, and its physiologically acceptable salt.

Figure 9:
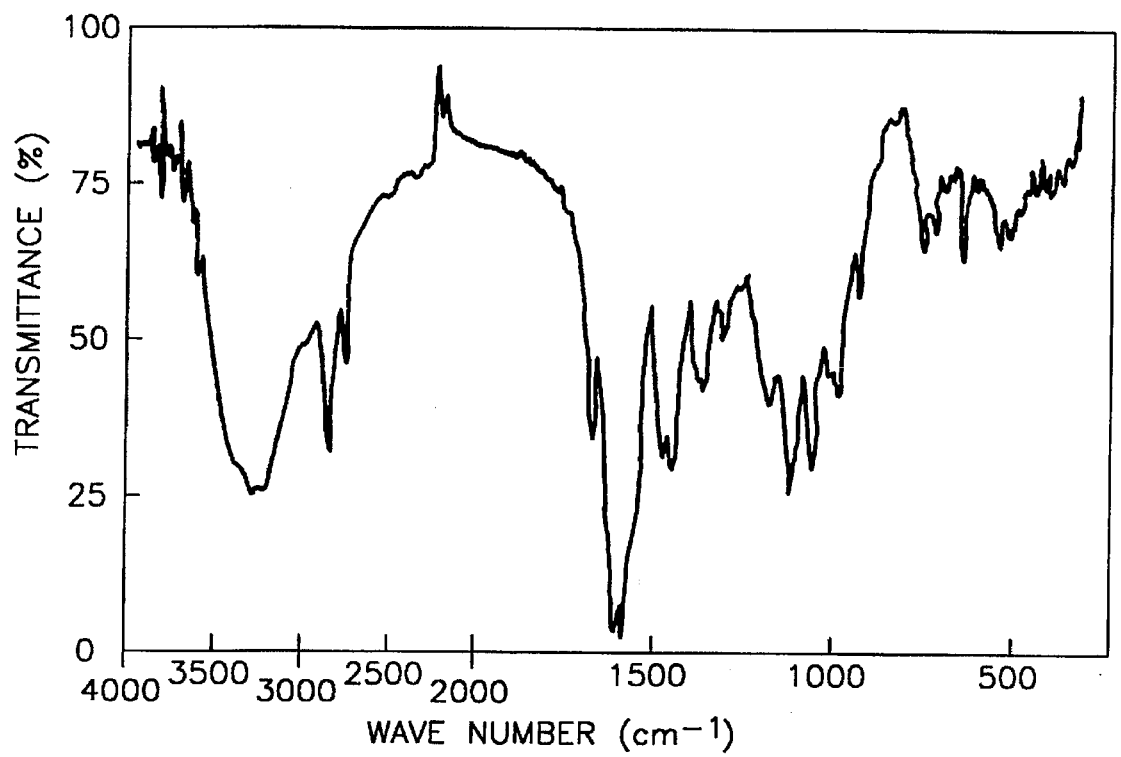
FIG. 9 shows the IR spectra of caledothricin D.

4. Caledothricin D having the following properties:
1) Appearance: white solid
2) Molecular weight (FAB-MS method):
   Positive ion mode: m/z 1355 (M+H)$^+$
   Negative ion mode: m/z 1353 (M−H)$^-$
3) Molecular formula: $C_{64}H_{98}N_{12}O_{20}$
4) IR spectrum: in KBr tablet (as shown in FIG. 9)
   Main absorption wavenumbers (cm$^{-1}$) are as follows:
   3342, 2910, 2830, 1740, 1655, 1527, 1204, 1140
5) $^1$H-NMR spectrum: 400 MHz, in mixture of dimethylsulfoxide-d$_6$ and trifluoroacetic acid (25:1), (as shown in FIG. 10.)
6) Solubility:
   Soluble: pyridine, trifluoroacetic acid,
   Sparingly soluble: water, dimethyl sulfoxide, methanol
7) Color reaction:
   Positive: anisaldehyde-sulphuric acid, HBr-ninhydrine, iodine vapor, molybdophosphoric acid, vanillin-sulphuric acid, Rydon-Smith reagent
   Negative: bromocresol green, ferric chloride, 2,4-dinitrophenyl-hydrazine-sulphuric acid, Sakaguchi reagent, silver nitrate
8) Thin-layer chromatography (TLC)

| Carrier | Solvent system | Rf |
|---|---|---|
| silica gel F254 | n-butanol:acetic acid:water (3:1:1) | 0.43 |

9) High performance liquid chromatography (HPLC)
   Carrier: >MCIgel<, manufactured by Mitsubishi Kasei Co.
   Mobile phase: acetonitrile: 10 mM sodium hydrogen phosphate buffer (pH 3.4) solvent gradient
   Flow rate: 1.2 ml/min. Rt=18.2±0.5 min
10) Classification of substance: amphoteric substance
11) Amino acid analysis: Caledothricin D was heated at 120° C. in 6N HCl for 24 hours, followed by subjecting to amino acid analysis to detect tyrosine, threonine×2, glutamine, glycine, histidine, and its physiologically acceptable salt.

5. Caledothricin E having the following physico-chemical properties:
1) Appearance: white solid
2) Molecular weight (FAB-MS method):
   Positive ion mode: m/z 1371 (M+H)$^+$
   Negative ion mode: m/z 1369 (M−H)$^-$
3) Molecular formula: $C_{64}H_{98}N_{12}O_{21}$
4) IR spectrum: in KBr tablet (as shown in FIG. 11)
   Main absorption wavenumbers (cm$^{-1}$) are as follows:
   3354, 2920, 2850, 1740, 1678, 1530, 1262, 1150–1050,
5) $^1$H-NMR spectrum: 400 MHz, in mixture of dimethylsulfoxide-d$_6$ and trifluoroacetic acid (25:1), (as shown in FIG. 12.)
6) Solubility:
   Soluble: pyridine, trifluoroacetic acid,
   Sparingly soluble: water, dimethyl sulfoxide, methanol
7) Color reaction:
   Positive: anisaldehyde-sulphuric acid, HBr-ninhydrine, iodine vapor, molybdophosphoric acid, vanillin-sulphuric acid, Rydon-Smith reagent
   Negative: bromocresol green, ferric chloride, 2,4-dinitrophenyl-hydrazine-sulphuric acid, Sakaguchi reagent, silver nitrate
8) Thin-layer chromatography (TLC)

| Carrier | Solvent system | Rf |
|---|---|---|
| silica gel F254 | n-butanol:acetic acid:water (3:1:1) | 0.39 |

9) High performance liquid chromatography (HPLC)
   Carrier: >MCIgel<
   Mobile phase: acetonitrile: 10 mM sodium hydrogen phosphate buffer (pH 3.4) solvent gradient
   Flow rate: 1.2 ml/min. Rt=17.6±0.5 min
10) Classification of substance: amphoteric substance
11) Amino acid analysis: Caledothricin E was heated at 120° C. in 6N HCl for 24 hours, followed by subjecting to amino acid analysis to detect tyrosine, threonine×2, glutamine, glycine, histidine, and its physiologically acceptable salt.

6. Caledothricin F having the following properties:

1) Appearance: white solid

2) Molecular weight (FAB-MS method):
Positive ion mode: m/z 1517 (M+H)$^+$
Negative ion mode: m/z 1515 (M−H)$^-$ 3) Molecular formula: $C_{70}H_{108}N_{12}O_{25}$ 4) IR spectrum: in KBr tablet (as shown in FIG. 13)
Main absorption wavenumbers (cm$^{-1}$) are as follows:
3356, 2926, 2855, 1740, 1657, 1518, 1260, 1100–1000, 5) $^1$H-NMR spectrum: 400 MHz, in mixture of dimethylsulfoxide-d$_6$ and trifluoroacetic acid (25:1) (as shown in FIG. 14.)

6) Solubility:
Soluble: pyridine, trifluoroacetic acid,
Sparingly soluble: water, dimethyl sulfoxide, methanol 7) Color reaction:
Positive: anisaldehyde-sulphuric acid, HBr-ninhydrine, iodine vapor, molybdophosphoric acid, vanillin-sulphuric acid, Rydon-Smith reagent
Negative: bromocresol green, ferric chloride, 2,4-dinitrophenyl-hydrazine-sulphuric acid, Sakaguchi reagent, silver nitrate 8) Thin-layer chromatography (TLC):

| Carrier | Solvent system | Rf |
|---|---|---|
| silica gel F254 | n-butanol:acetic acid:water (3:1:1) | 0.18 |

9) High performance liquid chromatography (HPLC)
Carrier: >MCIgel<,
Mobile phase: acetonitrile: 10 mM sodium hydrogen phosphate buffer (pH 3.4) solvent gradient
Flow rate: 1.2 ml/min. Rt=16.3±0.5 min 10) Classification of substance: amphoteric substance 11) Amino acid analysis: Caledothricin F was heated at 120° C. in 6N HCl for 24 hours, followed by subjecting to amino acid analysis to detect tyrosine, threonine×2, glutamine, glycine, histidine, and its physiologically acceptable salt.

7. Caledothricin G having the following properties:

1) Appearance: white solid

2) Molecular weight (FAB-MS method):
Positive ion mode: m/z 1373 (M+H)$^+$

3) Molecular formula: $C_{63}H_{96}N_{12}O_{22}$

Figure 16:
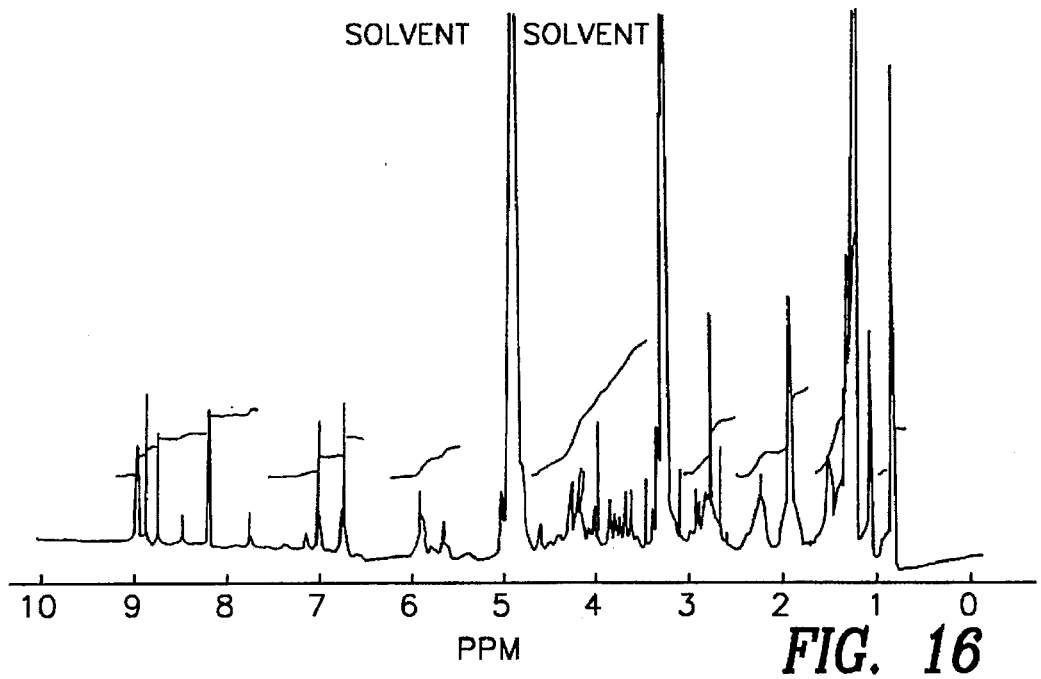
FIG. 16 shows the $^1$H-NMR spectra of caledothricin G.

4) IR spectrum: in KBr tablet (as shown in FIG. 15)
Main absorption wavenumbers (cm$^{-1}$) are as follows:
3350, 2926, 2855, 1739, 1659, 1518, 1265, 1120–1030, 5) $^1$H-NMR spectrum: 400 MHz, in mixture of dimethylsulfoxide-d$_6$ and trifluoroacetic acid (25:1), (as shown in FIG. 16.)

6) Solubility:
Soluble: pyridine, trifluoroacetic acid,
Sparingly soluble: water, dimethyl sulfoxide, methanol 7) Color reaction:
Positive: anisaldehyde-sulphuric acid, HBr-ninhydrine, iodine vapor, molybdophosphoric acid, vanillin-sulphuric acid, Rydon-Smith reagent
Negative: bromocresol green, ferric chloride, 2,4-dinitrophenyl-hydrazine-sulphuric acid, Sakaguchi reagent, silver nitrate 8) Thin-layer chromatography (TLC):

| Carrier | Solvent system | Rf |
|---|---|---|
| silica gel F254 | n-butanol:acetic acid:water (3:1:1) | 0.24 |

9) High performance liquid chromatography (HPLC):
Carrier: >MCIgel<
Mobile phase: Acetonitrile: 10 mM sodium hydrogen phosphate buffer (pH 3.4) solvent gradient
Flow rate: 1.2 ml/min. Rt=15.6±0.5 min 10) Classification of substance: amphoteric substance 11) Amino acid analysis: Caledothricin G was heated at 120° C. in 6N HCl for 24 hours, followed by subjecting to amino acid analysis to detect tyrosine, threonine×2, glutamine, glycine, histidine, and its physiologically acceptable salt.

8. Caledothricin H having the following properties:

1) Appearance: white solid

Figure 17:
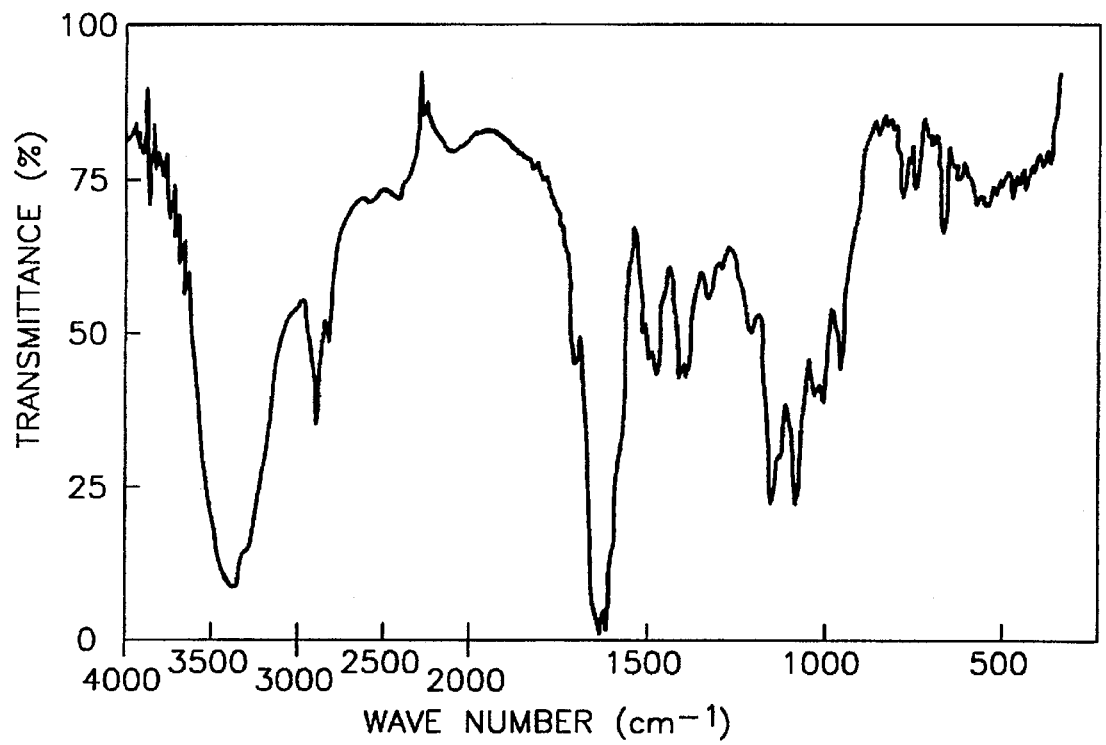
FIG. 17 shows the IR spectra of caledothricin H.

2) Molecular weight (FAB-MS method):
Positive ion mode: m/z 1343 (M+H)$^+$
Negative ion mode: m/z 1341 (M−H)$^-$ 3) Molecular formula: $C_{62}H_{94}N_{12}O_{21}$ 4) IR spectrum: in KBr tablet (as shown in FIG. 17)
Main absorption wavenumbers (cm$^{-1}$) are as follows:
3386, 2925, 2850, 1745, 1670, 1520, 1210, 1140

5) $^1$H-NMR spectrum: 400 MHz, in mixture of dimethylsulfoxide-d$_6$ and trifluoroacetic acid (25:1), (as shown in FIG. 18.)

6) Solubility:
Soluble: pyridine, trifluoroacetic acid,
Sparingly soluble: water, dimethyl sulfoxide, methanol 7) Color reaction:
Positive: anisaldehyde-sulphuric acid, HBr-ninhydrine, iodine vapor, molybdophosphoric acid, vanillin-sulphuric acid, Rydon-Smith reagent
Negative: bromocresol green, ferric chloride, 2,4-dinitrophenyl-hydrazine-sulphuric acid, Sakaguchi reagent, silver nitrate 8) Thin-layer chromatography (TLC):

| Carrier | Solvent system | Rf |
|---|---|---|
| silica gel F254 | n-butanol:acetic acid:water (3:1:1) | 0.22 |

9) High performance liquid chromatography (HPLC):
Carrier: >MCIgel<,
Mobile phase: Acetonitrile: 10 mM sodium hydrogen phosphate buffer (pH 3.4) solvent gradient
Flow rate: 1.2 ml/min. Rt=12.3±0.5 min 10) Classification of substance: amphoteric substance 11) Amino acid analysis: Caledothricin H was heated at 120° C. in 6N HCl for 24 hours, followed by subjecting to amino acid analysis to detect tyrosine, threonine×2, glutamine, glycine, histidine, and its physiologically acceptable salt.

9. Caledothricin I having the following physico-chemical properties:

1) Appearance: white solid

2) Molecular weight (FAB-MS method):

Positive ion mode: m/z 1327 (M+H)$^+$

Negative ion mode: m/z 1325 (M−H)$^−$

3) Molecular formula: $C_{62}H_{94}N_{12}O_{20}$

Figure 19:
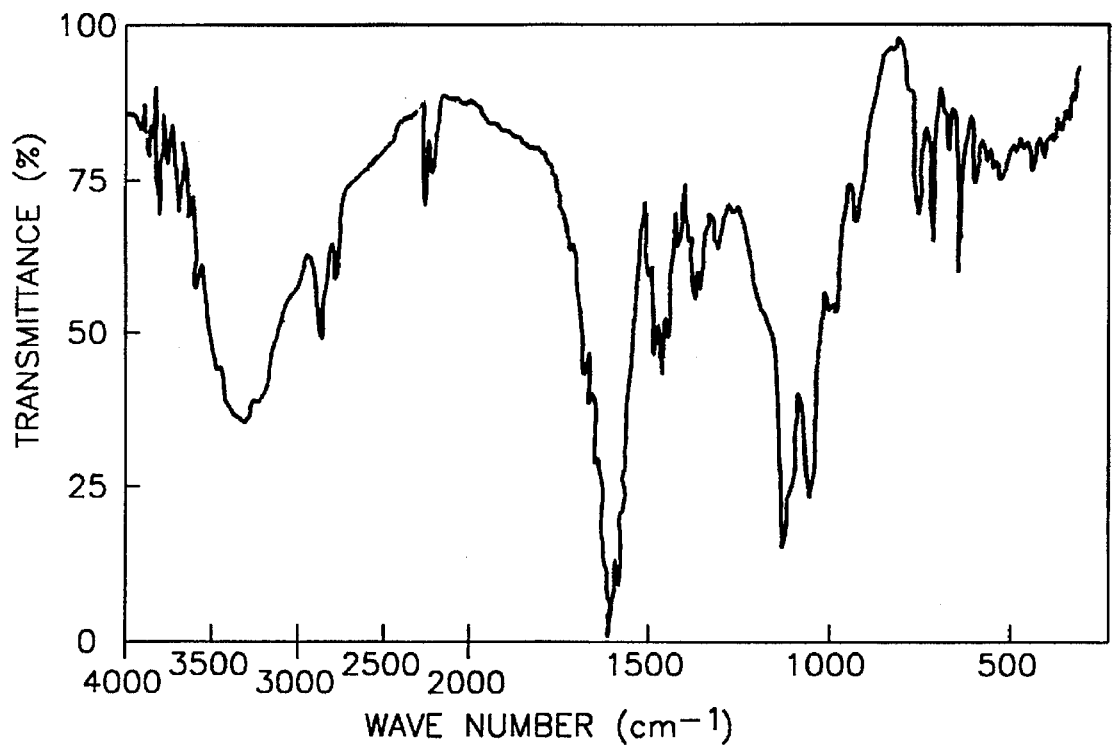
FIG. 19 shows the IR spectra of caledothricin I.

4) IR spectrum: in KBr tablet, (as shown in FIG. 19)

Main absorption wavenumbers (cm$^{-1}$) are as follows: 3347, 2920, 2850, 1679, 1540, 1205, 1140

5) $^1$H-NMR spectrum: 400 MHz, in mixture of dimethylsulfoxide-d$_6$ and trifluoroacetic acid (25:1), (as shown in FIG. 20)

6) Solubility:

Soluble: pyridine, trifluoroacetic acid,

Sparingly soluble: water, dimethyl sulfoxide, methanol

7) Color reaction:

Positive: anisaldehyde-sulphuric acid, HBr-ninhydrine, iodine vapor, molybdophosphoric acid, vanillin-sulphuric acid, Rydon-Smith reagent Negative: bromocresol green, ferric chloride, 2,4-dinitrophenyl-hydrazine-sulphuric acid, Sakaguchi reagent, silver nitrate 8) Thin-layer chromatography (TLC):

| Carrier | Solvent system | Rf |
| --- | --- | --- |
| silica gel F254 | n-butanol:acetic acid:water (3:1:1) | 0.43 |

9) High performance liquid chromatography (HPLC):

Carrier: >MCIgel<

Mobile phase: acetonitrile: 10 mM sodium hydrogen phosphate buffer (pH 3.4) solvent gradient Flow rate: 1.2 ml/min. Rt=12.6±0.5 min 10) Classification of substance: amphoteric substance 11) Amino acid analysis: Caledothricin I was heated at 120° C. in 6N HCl for 24 hours, followed by subjecting to amino acid analysis to detect tyrosine, threonine×2, glutamine, glycine, histidine, and its physiologically acceptable salt.

10. A pharmaceutical composition comprising an effective amount of at least one of caledothricin A, B, C, D, E, F, G, H, or I as defined in Claims 1–9, or salts thereof, and an inert carrier.

* * * * *